(12) United States Patent
Kyomoto

(10) Patent No.: US 9,907,656 B2
(45) Date of Patent: Mar. 6, 2018

(54) ANTIOXIDATIVE PROSTHETIC MEMBER

(71) Applicant: KYOCERA Medical Corporation, Osaka-shi, Osaka (JP)

(72) Inventor: Masayuki Kyomoto, Kyoto (JP)

(73) Assignee: KYOCERA CORPORATION, Kyoto-Shi, Kyoto (JP)

( * ) Notice: Subject to any disclaimer, the term of this patent is extended or adjusted under 35 U.S.C. 154(b) by 0 days.

(21) Appl. No.: 15/023,782

(22) PCT Filed: Oct. 3, 2014

(86) PCT No.: PCT/JP2014/076614
§ 371 (c)(1),
(2) Date: Mar. 22, 2016

(87) PCT Pub. No.: WO2015/053203
PCT Pub. Date: Apr. 16, 2015

(65) Prior Publication Data
US 2016/0213476 A1    Jul. 28, 2016

(30) Foreign Application Priority Data

Oct. 10, 2013 (JP) .................................. 2013-212921

(51) Int. Cl.
*A61F 2/28* (2006.01)
*A61F 2/30* (2006.01)
(Continued)

(52) U.S. Cl.
CPC ........ *A61F 2/30767* (2013.01); *A61F 2/2875* (2013.01); *A61L 27/16* (2013.01);
(Continued)

(58) Field of Classification Search
CPC ............................... A61L 27/16; A61F 2/2875
See application file for complete search history.

(56) References Cited

U.S. PATENT DOCUMENTS

| 5,115,814 A | 5/1992 | Griffith et al. |
| 2003/0212161 A1 | 11/2003 | McKellop et al. |

(Continued)

FOREIGN PATENT DOCUMENTS

| CN | 1556714 A | 12/2004 |
| CN | 101810884 A | 8/2010 |

(Continued)

OTHER PUBLICATIONS

International Preliminary Report on Patentability, PCT/JP2014/076614, dated Apr. 12, 2016, 8 pgs.

(Continued)

*Primary Examiner* — David Isabella
*Assistant Examiner* — Suba Ganesan
(74) *Attorney, Agent, or Firm* — Volpe and Koenig, P.C.

(57) ABSTRACT

To provide a prosthetic member that is less likely to degrade its mechanical properties even when using it in the presence of squalene, and a method of producing the same. The prosthetic member in the present invention includes a substrate exhibiting excellent antioxidant properties and including an antioxidant and a polymer material, and a polymer film(s) covering a surface of the substrate and comprising a (meth)acrylate compound. The method for producing the prosthetic member in the present invention includes the steps of: forming a substrate comprising an antioxidant and a polymer material, cleaning a surface of the substrate with a cleaning liquid, and covering the cleaned surface of the substrate with a polymer film(s) comprising a (meth)acrylate compound.

16 Claims, 9 Drawing Sheets

(51) Int. Cl.
  A61L 27/16    (2006.01)
  A61L 27/34    (2006.01)
  A61L 27/50    (2006.01)
  A61L 27/54    (2006.01)

(52) U.S. Cl.
  CPC ............. *A61L 27/34* (2013.01); *A61L 27/505* (2013.01); *A61L 27/54* (2013.01); *A61F 2210/0076* (2013.01); *A61L 2300/428* (2013.01); *A61L 2420/02* (2013.01)

(56) References Cited

U.S. PATENT DOCUMENTS

| | | | |
|---|---|---|---|
| 2004/0243249 A1 | 12/2004 | Ishihara et al. | |
| 2005/0119746 A1 | 6/2005 | Lidgren | |
| 2009/0324669 A1 | 12/2009 | Ogawa et al. | |
| 2010/0032090 A1* | 2/2010 | Myung | A61L 27/48 427/2.26 |
| 2011/0028600 A1* | 2/2011 | Rufner | A61L 27/16 523/351 |
| 2015/0141545 A1 | 5/2015 | Kyomoto et al. | |

FOREIGN PATENT DOCUMENTS

| | | |
|---|---|---|
| CN | 103212110 A | 7/2013 |
| EP | 2856978 A1 | 4/2015 |
| JP | H05-502171 | 4/1993 |
| JP | 2003-530957 A | 10/2003 |
| JP | 2007-089842 A | 4/2007 |
| JP | 2009-544411 A | 12/2009 |
| JP | 2011-087973 A | 5/2011 |
| JP | 3181095 U | 1/2013 |
| WO | 2010/135526 A2 | 11/2010 |
| WO | 2013/180228 A1 | 12/2013 |

OTHER PUBLICATIONS

Kyomoto, M., et al., "Enhanced wear resistance of orthopaedic bearing due to the cross-linking of poly (MPC) graft chains induced by gamma-ray irradiation," J Biomed Mater Res Pt B Appl Biomater, 2008, vol. 84, No. 2, pp. 320-327, (with English reference).

Kyomoto, M., et al., "Development of innovative artificial joints modified with a high lubricious phospholipid polymer," Materials Integration, 2007, vol. 20, No. 9, pp. 28-32, (with English Abstract).

Tomita, N., et al., "Prevention of fatigue cracks in ultrahigh molecular weight polyethylene joint components by the addition of vitiamin E," J Biomed Mater Res., 1999, vol. 48, No. 4, pp. 474-478, (with English reference).

Oral, E., et al., "The Effect of alpha-tocopherol on the oxidation and free radical decay in irradiated UHMWPE," Biomaterials, 2006, vol. 27, No. 32, pp. 5580-5587, (with English reference).

Reno, F., et al., "UHMWPE and vitamin E bioactivity: an emerging perspective," Biomaterials, 2006, vol. 27, No. 16, pp. 3039-3043 (with English reference).

Oral, E., et al., "A new mechanism of oxidation in ultrahigh molecular weight polyethylene caused by squalene absorption," J Biomed Mater Res Pt B Appl Biomater, 2012, vol. 100, No. 3, pp. 742-751, (with English reference).

Sawano, H., et al., "Study on wear reduction mechanism of artificial joints grafted with hydrophilic polymer membranes," Wear, 2010, vol. 268, No. 1-2, pp. 233-240, (with English reference).

Sakota, H., et al., "Discussion Regarding Degradation Mechanism of Ultrahigh Molecular Weight Polyethylene by Squalene," Proceedings of Symposium 2012 of the Japanese Society for Biomaterials, p. 223[PC2], (with Partial English Translation).

International Search Report, PCT/JP2014/076614, dated Dec. 22, 2014, 2 pgs.

Chinese Office Action with English concise explanation and translation, Chinese Patent Application No. 201480055344.0, dated May 9, 2017, 11 pgs.

Extended European Search Report, European Patent Application No. 14852833.4, dated May 11, 2017, 11 pgs.

Kyomoto, M., et al., "Poly(2-methacryloyloxyethyl phosphorylcholine) grafting and vitamin E blending for high wear resistance and oxidative stability of orthopedic bearings," Biomaterials 35 (2014), pp. 6677-6686.

Kyomoto, M., et al., "A hydrated phospholipid polymer-grafted layer prevents lipid-related oxidative degradation of cross-linked polyethylene," Biomaterials 112 (2017), pp. 122-132.

Japanese Office Action with English concise explanation, Japanese Patent Application No. 2013-212921, Oct. 10, 2017, 5 pgs.

\* cited by examiner

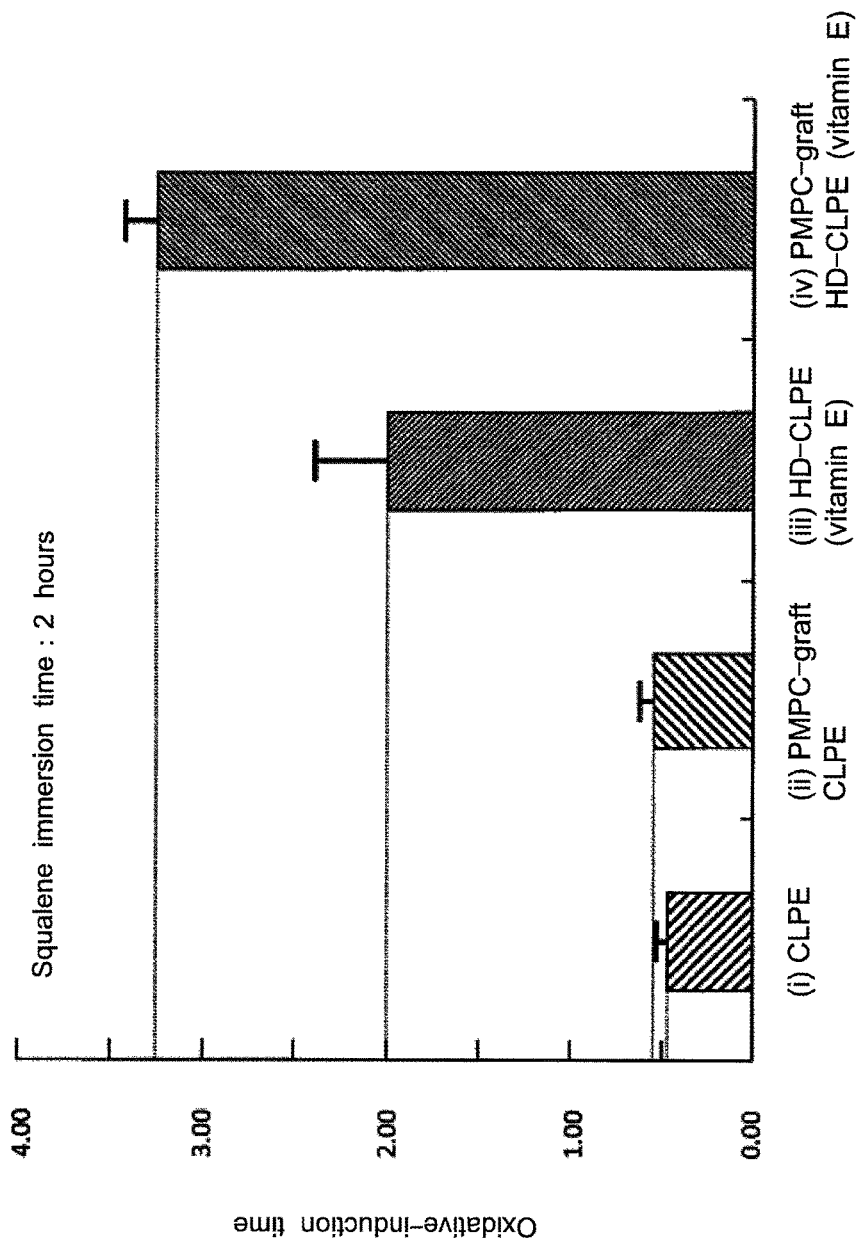

ANTIOXIDATIVE PROSTHETIC MEMBER

TECHNICAL FIELD

The present invention relates to prosthetic members having excellent antioxidative properties, and more particularly to a prosthetic member having excellent antioxidative properties that is used to repair damage to the cranial bones, joints and the like.

BACKGROUND ART

Conventionally, a defect in the cranial bone has been repaired by a prosthetic member for cranial bones (cranial bone plate). The cranial bone plate is formed from safety material. Examples of known safety materials include ceramic materials (apatite-based ceramics, alumina ceramics, zirconia ceramics, etc.), metal materials (titanium, titanium alloys, cobalt-chromium alloys, stainless steel, etc.) and polymer materials (polymethyl methacrylate, polyether ether ketone, polyethylene, etc.) (see, for example, Patent Documents 1 and 2).

In particular, ultrahigh molecular weight polyethylene (UHMWPE) has excellent properties, including its light weight, high strength, excellent impact resistance and good formability, and thus UHMWPE is a promising material for the cranial bone plate.

PRIOR ART DOCUMENT

Patent Documents

Patent Document 1: JP 2007-89842 A
Patent Document 2: JP utility model No. 3181095

SUMMARY OF THE INVENTION

Problems to be Solved by the Invention

The prosthetic member, such as a cranial bone plate, is in contact with biological fluid for a long time, and thus may be in contact with substances included in the biological fluid to adsorb or absorb these substances. Study results show that, when UHMWPE not including free radicals adsorbs or absorbs squalene, cholesterol or esterified fatty acid included in the biological fluid, mechanical properties of the prosthetic member, such as compressive strength and elastic modulus, are degraded (see Evan S. Greenbaum et al., "Effect of lipid absorption on wear and compressive properties of unirradiated and highly crosslinked UHMWPE: An in vitro experimental model", Biomaterials 25 (2004) pp. 4479-4484).

That is, when the prosthetic member including a substrate formed from polymer material such as UHMWPE is implanted into a living body, the substrate might adsorb or absorb squalene and the like in the biological fluid to deteriorate mechanical properties thereof even if the substrate does not include free radicals. If the mechanical properties are degraded beyond an allowable limit, the implanted prosthetic member must be replaced with a new one.

An object of the present invention is to provide a prosthetic member that is less likely to degrade its mechanical properties when using it in the presence of squalene, and a method of producing the same.

Means for Solving the Problems

The inventors have intensively studied to solve the foregoing problems and, as a result, have found that the mechanical properties of a prosthetic member are degraded due to oxidation, and that since squalene tends to promote such an oxidation reaction, the mechanical properties of the prosthetic member are drastically degraded in the presence of squalene. Based on these findings, the present invention has been made.

The prosthetic member according to the present invention, which has excellent antioxidative properties, comprises:
a substrate comprising an antioxidant and a polymer material; and
a polymer film(s) covering a surface of the substrate and comprising a (meth)acrylate compound.

A method of producing a prosthetic member having excellent antioxidative properties according to the present invention comprises steps of:
forming a substrate comprising an antioxidant and a polymer material;
cleaning a surface of the substrate with a cleaning liquid; and
covering the cleaned surface of the substrate with a polymer film(s) comprising a (meth)acrylate compound.

Effects of the Invention

Accordingly to the prosthetic member of the present invention, it is possible to obtain a prosthetic member that exhibits excellent antioxidative properties by including the antioxidant in the substrate. Furthermore, the surface of the substrate is covered with the polymer film(s) comprising a (meth)acrylate compound, thereby enabling suppression of the adsorption or absorption of squalene. As a result, a promoting effect of the oxidation reaction due to squalene can be suppressed. Thus, the antioxidative properties of the prosthetic member can be effectively improved. That is, since the prosthetic member includes both the substrate which includes the antioxidant, and the polymer film(s) which covers the surface of the substrate, the prosthetic member, that is less likely to degrade its mechanical properties even when using it in the presence of squalene, can be obtained.

According to the method of producing the prosthetic member of the present invention, the cleaning step is included, thereby enabling improvement of adhesiveness of the polymer film(s) to the substrate, thus producing the prosthetic member having excellent antioxidative properties.

In this way, the present invention can suppress the adsorption or absorption of squalene and the like in the substrate of the prosthetic member.

BRIEF DESCRIPTION OF THE DRAWINGS

FIGS. 2A, 2B, and 2C are schematic diagrams of the cranial bone plate in the first embodiment, in which FIG. 2A is a front view thereof, FIG. 2B is a side view from the direction of the arrow (b) in FIG. 2A, and FIG. 2C is a side view from the direction of the arrow (c) in FIG. 2A.

FIGS. 5A and 5B are diagrams for explaining an FTIR measurement method in Example 1, in which FIG. 5A is a schematic perspective view of a sample for measurement, and FIG. 5B is a front view of a sample piece for measurement.

FIG. 9 is a bar graph showing the result of an oxidative induction experiment in Example 2.

MODE FOR CARRYING OUT THE INVENTION

Figure 1:
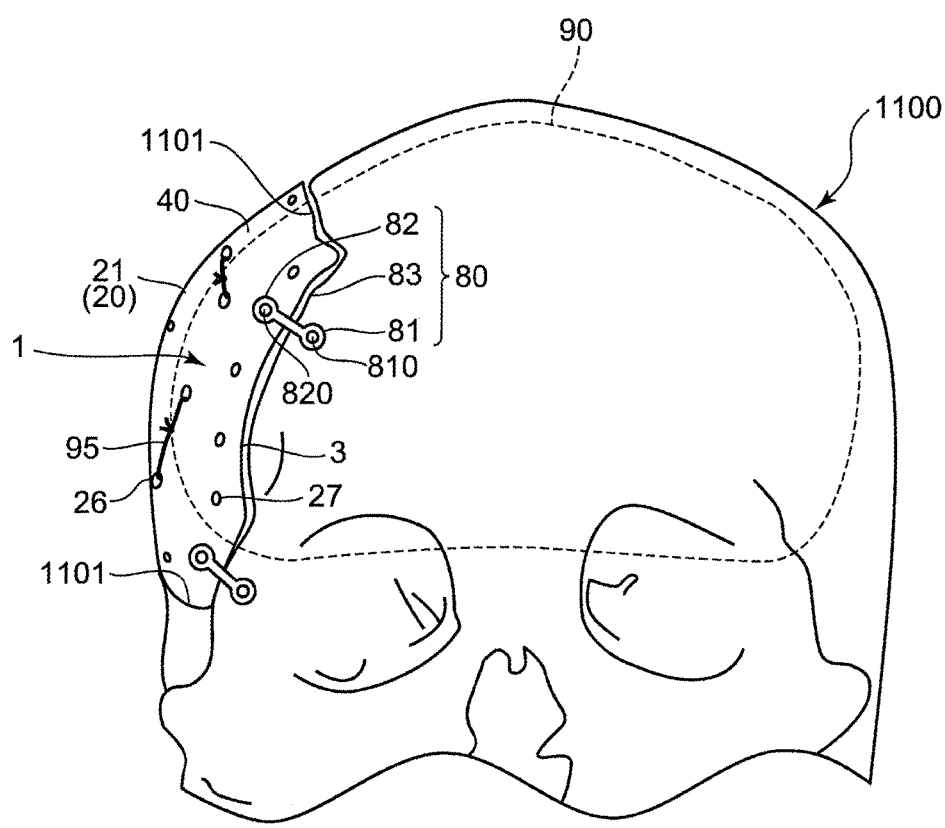
FIG. 1 is a schematic diagram for explaining a state in which a cranial bone plate according to a first embodiment is fixed at a defect of a cranial bone.
Figure 2A:
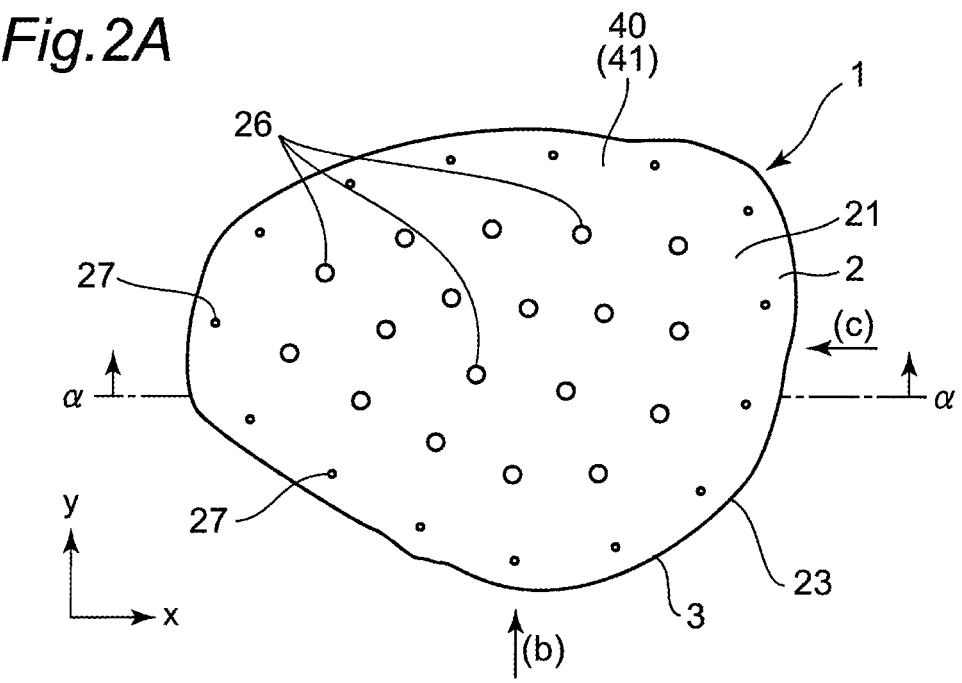
Figure 2B:
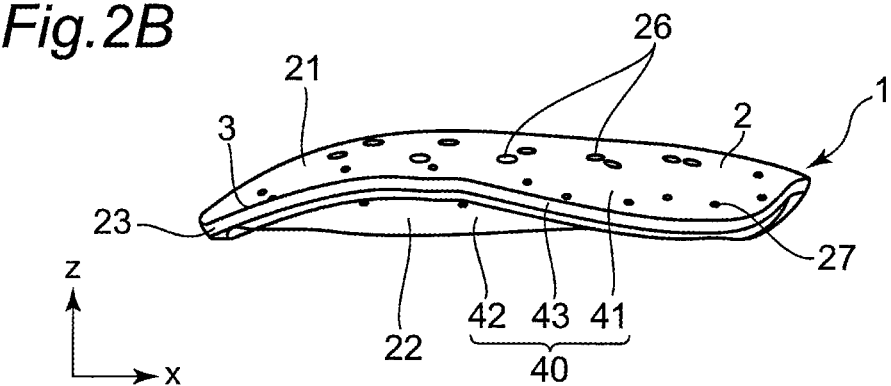
Figure 2C:
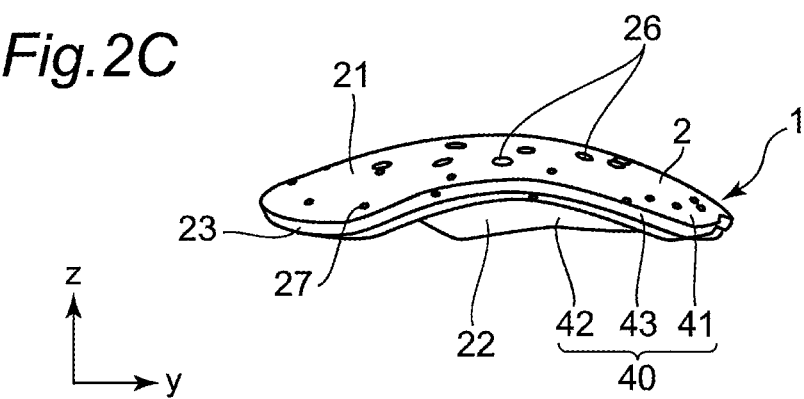

Embodiments of the present invention will be described in detail below with reference to the accompanying drawings. In the description below, the terms indicative of specific directions or positions (for example, the terms "upper", "lower", "right", and "left", and other terms including these terms) are used as needed. The use of these terms is to make the present invention easily understood with reference to the figures, and the meanings of these terms are not intended to limit the technical scope of the present invention. Parts represented by the same reference character in the figures indicate the same part or member.

First Embodiment

In this embodiment, a prosthetic member according to the present invention will be described in detail below by taking a cranial bone plate 1 as an example.

The cranial bone plate 1 in this embodiment as shown in FIG. 1 is the prosthetic member that serves to cover a defect 1101 of a cranial bone 1100 caused by brain surgery, cranial bone fracture and the like. A brain 90 inside the cranial bone 1100 can be protected by the cranial bone plate 1. The cranial bone 1100 shown in FIG. 1 is covered with a scalp.

As shown in FIGS. 1 and 2A to 2C, the cranial bone plate 1 has an outer surface 21 disposed on a side of the scalp, an inner surface 22 disposed on a side of the brain 90, and an outer peripheral surface 23 through which the inner surface 22 is connected with the outer surface 21 at an outer periphery 3 of the cranial bone plate 1. The cranial bone plate 1 is provided with two kinds of holes (through holes 26 and screw holes 27) that penetrate from the inner surface 22 to the outer surface 21. The screw holes 27 are formed in the vicinity of the outer periphery 3 of the cranial bone plate 1 and used to fix the cranial bone plate 1 to the cranial bone 1100. The through holes 26 are formed on the inner side of the screw holes 27 and used to fix, to the cranial bone plate 1, a dura mater that extends between the brain 90 and the cranial bone 1100 to wrap the brain 90.

Figure 3A:
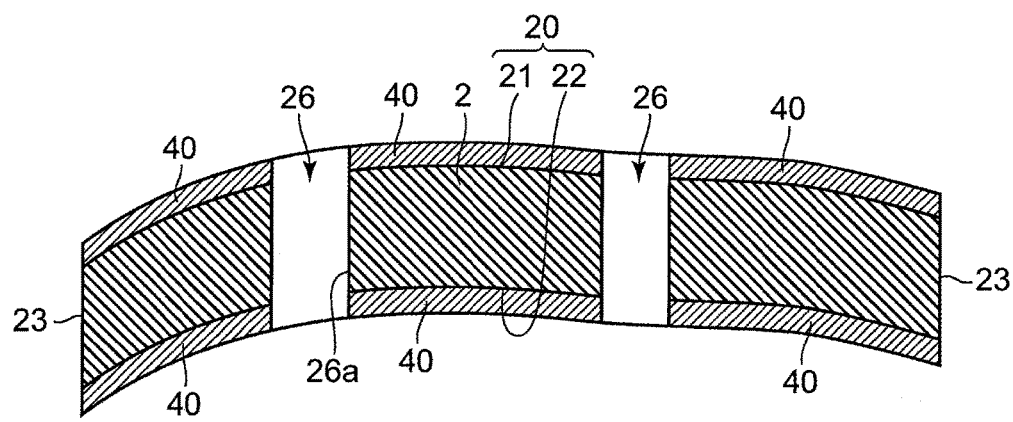
FIGS. 3A and 3B are schematic cross-sectional views taken along the line α-α line of FIG. 2A.
Figure 3B:
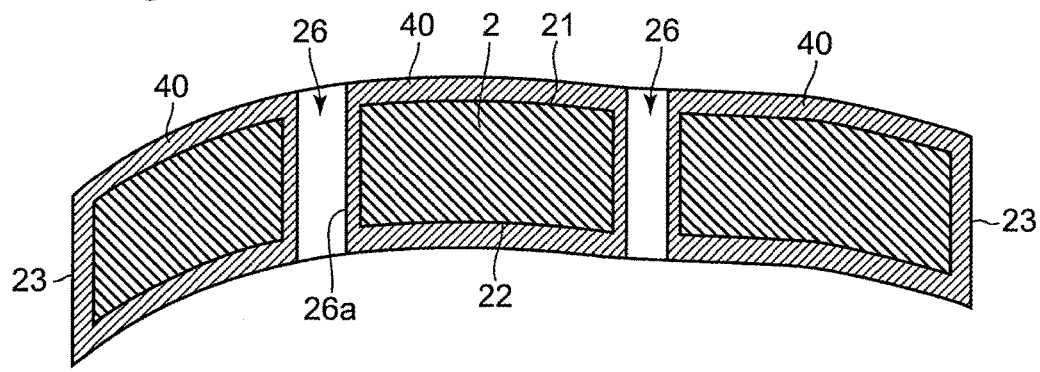
Figure 3B:
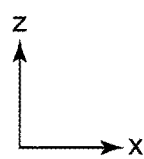

FIGS. 3A and 3B are cross-sectional views of the cranial bone plate 1 in this embodiment. To easily understand respective components, FIGS. 3A and 3B emphasize the thickness of each component and the like.

The cranial bone plate 1 shown in FIG. 3A includes a substrate 2, and polymer film(s) 40 covering the surfaces 20 (outer surface 21 and inner surface 22) of the substrate 2.

The substrate 2 used in the cranial bone plate 1 includes polymer material and an antioxidant. The term "antioxidant" as used in the present specification means an additive for improving the antioxidative properties of the polymer material. The antioxidant has the capacity of inactivating causative substances that induce oxidation (active oxygen and the like). The polymer materials used for the substrate 2 may include, for example, a polyethylene (PE)-based material.

The substrate 2 can include any material other than the polymer material and the antioxidant, but can be formed of only the polymer material and the antioxidant.

The "material for the substrate" forming the substrate 2 of the cranial bone plate 1 includes the polymer material and the antioxidant to provide the antioxidative properties due to the antioxidant as the mechanical properties of the polymer material. After implanting the cranial bone plate 1 in the living body, when the substrate 2 of the cranial bone plate 1 comes into contact with causative substances that induce oxidation (active oxygen and the like), the causative substances can be inactivated. In this way, the oxidation degradation of the substrate 2 can be suppressed.

The polymer film(s) 40 covering the surface 20 of the substrate 2 is formed of a polymer including a (meth)acrylate compound. In more detail, the polymer film(s) 40 has the structure in which polymer chains comprising a (meth)acrylate compound are arranged on the surface of the substrate 2.

It should be understood that "a polymer comprising a (meth)acrylate compound", "a polymer film(s) comprising a (meth)acrylate compound", and "a polymer chain comprising a (meth)acrylate compound" as used herein include not only a member consist of a (meth)acrylate compound alone, but also a variety of compounds comprising a (meth)acrylate compound and other polymerizable compounds.

As mentioned above, study results show that the mechanical properties of the UHMWPE are degraded by squalene, cholesterol, esterified fatty acid or the like included in the biological fluid existing in the living body. The inventors of the present application have found that the reason for this is that squalene or the like promotes the oxidation reaction of polymer materials. Furthermore, it is found that the effect of promoting the oxidation reaction by squalene and the like can be suppressed by covering the surface of the substrate 2 with the polymer film(s) 40 comprising a polymer of the (meth)acrylate compound. It is assumed that, the covering of the surface 20 of the substrate 2 with the polymer film(s) 40 inhibits adsorption or absorption of squalene and the like in the surface 20 of the substrate 2, resulting in less diffusion of squalene and the like into the substrate 2, thus suppressing the effect of promoting the oxidation reaction by squalene and the like.

A polymer material formed by polymerizing a (meth)acrylate compound is least soluble in squalene and the like. Since the polymer film(s) 40 comprising the (meth)acrylate compound is formed on the surface of the substrate 2, the polymer film(s) 40 is less likely to be dissolved in and removed by squalene when the cranial bone plate 1 comes into contact with squalene. Accordingly, the effect of suppressing the diffusion of squalene and the like into the substrate 2 can be continued for a long time.

In particular, the polymer film(s) 40 comprising the (meth)acrylate compound preferably has low solubility in squalene and the like. Specifically, the polymer film(s) 40 is preferably poorly-soluble in squalene at a 100% concentration (at a solubility of 3 g/100 g to 0.01 g/100 g in 100% squalene), very poorly-soluble (at a solubility of 0.1 g/100 g to 0.01 g/100 g in 100% squalene), or insoluble (at a solubility of 0.01 g/100 g or less in 100% squalene). The polymer film(s) 40 is more preferably very poorly-soluble or insoluble, and is most preferably the insoluble polymer film(s) 40.

The (meth)acrylate compound suitable for use in the present invention is one whose safety has been already confirmed.

Preferably, the (meth)acrylate compound has hydrophilicity, and it can be supposed to improve the effect of suppressing the penetration of squalene or the like into the substrate 2 for the following reason. When the (meth) acrylate compound has hydrophilicity (for example, when an end group of the compound has a hydrophilic group and the like), the polymer film(s) 40 formed from the (meth) acrylate compound also has hydrophilicity. Since the hydrophilic polymer film(s) 40 holds water in the living body, a water layer is formed on the surface of the polymer film(s) 40. This water layer can suppress the penetration of lipid such as squalene, cholesterol and an esterified fatty acid that has hydrophobicity. That is, the polymer film(s) 40 of the cranial bone plate 1 preferably includes the hydrophilic (meth)acrylate compound because the effect of suppressing the penetration of lipid such as squalene, into the substrate 2 is enhanced.

Further, the polymer film(s) 40, which includes a phosphorylcholine group, has the structure similar to that of a biomembrane (see, Ishihara: Surgery, Vol. 61, p. 132 (1999)). Thus, the polymer film(s) 40 preferably includes a compound with a phosphorylcholine group. Examples of the (meth)acrylate compound having a phosphorylcholine group include 2-methacryloyloxyethyl phosphorylcholine, 2-acryloyloxyethyl phosphorylcholine, 4-methacryloyloxybutyl phosphorylcholine, 6-methacryloyloxyhexyl phosphorylcholine, ω-methacryloyloxyethylene phosphorylcholine, and 4-styryloxybutyl phosphorylcholine. In particular, 2-methacryloyloxyethyl phosphorylcholine (hereinafter referred to as a MPC) can be exemplified. 2-methacryloyloxyethyl phosphorylcholine (hereinafter referred to as MPC) is particularly preferable.

Absorption of squalene in UHMWPE is disclosed in a document by Oral et al. (Ebru Oral et al., "A new mechanism of oxidation in ultrahigh molecular weight polyethylene caused by squalene absorption", Journal of Biomedical Materials Research Part B: Applied Biomaterials 100 (2012) pp. 742-751). This document defines "squalene index" that indicates the degree of absorption of squalene in UHMWPE material. The squalene index indicates a relative amount of absorption of squalene, which is the ratio between an area of a peak corresponding to polyethylene (in the peak position at 1895 $cm^{-1}$) and an area of a peak corresponding to squalene (in the peak position at 1145 $cm^{-1}$), the peak areas being determined from a measurement spectrum by the FTIR. In detail, the peak area of polyethylene ($A_{1895}$) is determined from an area of the FTIR spectrum in a range of 1,850 $cm^{-1}$ to 1,985 $cm^{-1}$, and the peak area of squalene ($A_{1145}$) is determined from an area of the FTIR spectrum in a range of 1,134 $cm^{-1}$ to 1,168 $cm^{-1}$. The squalene index is calculated as the "squalene index=(squalene peak area $A_{1145}$/polyethylene peak area $A_{1895}$)".

According to the results obtained by Oral et al., when the UHMWPE sample is immersed in squalene at 120° C. for 2 hours, the surface of the UHMWPE sample has a squalene index of approximately 0.2 to 0.25. In contrast, in the present invention, the surface 20 of the cranial bone plate 1 after being immersed in squalene at 120° C. for 2 hours preferably has a squalene index of 0.15 or less. Thus, the amount of absorption of squalene can be reduced to suppress the oxidation reaction of the substrate 2 due to the absorption of squalene.

An "oxidative-induction time (OIT)" is known as an index of oxidability of a polymer material and the like (ref. ASTM/D3895-07). The oxidative-induction time indicates the time, from switching an atmospheric gas from nitrogen ($N_2$) to oxygen ($O_2$), to observing heat generation by a differential scanning calorimeter (DSC) due to the start of oxidation of a sample. It can be found that, the longer the OIT, the less susceptible to oxidation the material is (that is, the material has higher antioxidative properties).

In the cranial bone plate 1 of the present invention in the present application, the oxidative-induction time ($T_0$) of the (non-immersed) cranial bone plate 1 not immersed in a squalene liquid is preferably 2 minutes or more. The normal UHMWPE has an oxidative-induction time of about 0.5 minutes, which is very short. On the other hand, the cranial bone plate 1 has the oxidative-induction time of 2 minutes or more and has four times higher oxidative-induction time than usual, and thereby can have extremely excellent antioxidative properties.

In acceleration experiments including immersion into a squalene liquid at a high concentration, the oxidative-induction time ($T_{0.5}$) of the cranial bone plate 1 after being immersed in a squalene liquid at 100% concentration for 0.5 hour is preferably 50% or more (that is, $T_{0.5}$ is 1 minute or more) of the oxidative-induction time $T_0$ obtained when not being immersed. Further, the oxidative-induction time ($T_2$) of the cranial bone plate 1 after being immersed in squalene liquid for 2 hours is preferably 30% or more (that is, $T_2$ is 0.6 minutes or ore) of the oxidative-induction time $T_0$ obtained when not being immersed.

In this way, when $T_{0.5}$ is 50% or more of $T_0$, and/or $T_2$ is 30% or more of $T_0$, the oxidative-induction time can also be kept relatively high after installing the cranial bone plate in the living body for a long time. In particular, even after 2 hours, the oxidative-induction time can be kept higher than an oxidative-induction time (of about 0.5 minutes) of a normal UHMWPE.

Note that even if the antioxidative properties are reduced, this does not mean that the strength is reduced at the same rate. That is, if the antioxidative properties of the cranial bone plate 1 are reduced to 50% or 30% of the antioxidative properties before use, this does not mean that the mechanical properties of the cranial bone plate 1 are not reduced to 50% or 30%. Thus, when the antioxidative properties are reduced to 50% or 30%, UHMWPE does not break due to the oxidation and degradation, and the mechanical properties can be kept sufficiently high.

In the cranial bone plate 1 shown in FIG. 3B, more preferably, the polymer film(s) 40 covers not only the surfaces 20 (outer surface 21 and inner surface 22) of the substrate 2, but also the outer peripheral surface 23.

As mentioned above, the polymer film(s) 40 is supposed to have the function of suppressing the substrate 2 from adsorbing or absorbing squalene and the like. Thus, the inner surface 22 and outer surface 21 that have wide areas and are more likely to be affected by adsorption or absorption of squalene are desirably covered by the polymer film(s) 40. When the outer peripheral surface is also covered with the polymer film(s) 40, more preferably, the influences of adsorption and absorption of squalene can be further suppressed.

Furthermore, when inner side surfaces 26a of the through holes 26 and inner side surfaces (not shown) of the screw holes 27 that are provided in the cranial bone plate 1 are also covered with the polymer film(s) 40, preferably, the influence of adsorption of squalene can be suppressed much more.

Here, the functions of a plurality of holes (through holes 26 and screw holes 27) provided in the cranial bone plate 1 will be described.

The screw hole 27 is used to cause a screw to be threaded thereinto when fixing the cranial bone plate 1 to the cranial bone 1100. As shown in FIG. 1, the cranial bone plate 1 can be fixed using a metal plate 80 for fixing. The metal plate 80 exemplified in FIG. 1 includes two fixing portions 81 and 82 and a strip-shaped member 83 connecting these fixing portions. Each of the fixing portions 81 and 82 is provided with a hole for insertion of the screw.

To fix the cranial bone plate 1 to the cranial bone 1100 by the metal plates 80, the first fixing portion 81 is fixed to the cranial bone 1100 by a bone screw 810, and the second fixing portion 82 is fixed to the screw hole 27 in the cranial bone plate 1 with a screw 820. Thus, the cranial bone 1100 and the cranial bone plate 1 are connected together by the strip-shaped members 83 of the metal plates 80.

In this way, the use of a plurality of metal plates 80 for fixing connects the cranial bone plate 1 with the cranial bone 1100, which can stabilize the cranial bone plate 1 to fix the cranial bone plate to the cranial bone 1100.

The through holes 26 are used to fix the dura mater for covering the brain 90, to the cranial bone plate 1. The dura mater is a hard membrane that holds the brain 90 and is normally conglutinated to the inner surface of the cranial bone 1100. However, the cranial bone plate 1 fitted into the defect 1101 is not conglutinated to the dura mater, causing the dura mater to sag. For this reason, the dura mater needs to be fixed to the cranial bone plate 1 to be pulled up. In general, the use of a suture fixes the dura mater to the cranial bone plate 1 in a range of the defect 1101 of the cranial bone 1100.

When performing an operation on the brain 90, the dura mater peeled off from the cranial bone 1100 is cut and opened to expose the brain 90. After completion of the operation, the cut part of the dura mater is sutured with a suture 85 to cover the defect 1101 with the cranial bone plate 1. At this time, both ends of the suture 85 that sutures the dura mater are inserted into two adjacent through holes 26 of the plurality of through holes provided in the cranial bone plate 1 from the inner surface 22 side to the outer surface 21 side. After fixing the cranial bone plate 1 to the cranial bone 1100, both ends of the suture 85 are ligated at the outer surface 21 side of the cranial bone plate 1. In this way, the dura mater can be fixed to the cranial bone plate 1 to be pulled up.

Next, a method for producing a prosthetic member (cranial bone plate 1) according to the present invention will be described. The production method for the cranial bone plate 1 includes the steps of:

Step 1. step of forming a substrate 2;

Step 2. step of cleaning the surfaces 20 of the substrate 2; and

Step 3. step of forming a polymer film(s) 40 on the surfaces 20.

Note that between step 1 and step 2, a crosslinking step (crosslinking steps 1-A and 1-B) may be provided for forming crosslinks between polymer materials included in the substrate 2.

The respective steps will be described in detail below.
(Step 1. Step of Forming Substrate 2)

In step 1, the substrate 2 including the antioxidant and the polymer material is formed. Formation means suitable for use can include a processing method that involves preparing a block of material for the substrate including the antioxidant and polymer material, and cutting the block-shaped material for the substrate into the shape of substrate 2. The block-shaped material for the substrate can be produced, for example, by mixing powdery, granular, or pellet-shaped polymer material (e.g., ultrahigh molecular weight PE (UHMWPE) material, and an antioxidant (liquid or powdery), and forming the thus-obtained mixture by compaction molding, extrusion, or injection molding. When using UHMWPE as the polymer material, UHMWPE is a thermoplastic resin, but has low fluidity even at a melting temperature or higher. For this reason, the solid (powdery or granular) UHMWPE may be introduced into a die and molded under high temperature and pressure.

Here, the compaction molding can include, for example, a cold pressing stage, a pressure-drop and temperature-rise stage, a high-temperature and high-pressure maintaining stage, and a cooling stage.

In the cold pressing stage, raw material powder comprising a mixture of UHMWPE and the antioxidant is introduced into a molding die, and then compressed (pressed) under a pressure of 200 to 250 MPa at a temperature 25° C. (at the room temperature) for one to 10 minutes.

In the pressure-drop and temperature-rise stage, the pressure applied to the die is dropped from a value set in the cold pressing stage to 20 to 35 MPa, and the temperature of the die is raised from 25° C. to 140 to 275° C. This stage is held for 10 to 40 minutes.

In the high-temperature and high-pressure maintaining stage, while the temperature of the die is kept at the high temperature set in the pressure-drop and temperature-rise stage, the pressure of the die is increased from a value set in the pressure-drop and temperature-rise stage to 100 to 180 MPa, and then this stage is held for 1 to 10 minutes.

In the cooling stage, while the pressure of the die is kept at the value set in the high-temperature and high-pressure maintaining stage, the temperature of the die is gradually cooled over 10 to 50 minutes from the value set in the high-temperature and high-pressure maintaining stage to 25° C. (room temperature).

Finally, the pressure of the die is released, and a compaction of the raw material powder is taken out of the die to obtain a compaction-molded body. The compaction-molded body obtained in this manner includes an antioxidant, such as vitamin E.

The material for the substrate obtained by the compaction molding, extrusion, or injection molding can be shaped by the cutting process and then subjected to a polymer film(s) formation process.

A molding method in which the mixed powder is compacted molded or injection molded in the shape of the substrate 2 (so-called near-net-shape molding method) can also be used. The substrate 2 molded by the near-net-shape molding method does not need the cutting process, or needs only slight cutting, thereby reducing the cost and labor required for the cutting process.

The cranial bone plate 1 can be made to order for each patient according to the shape or dimension of a different defect. Prior to the operation, three-dimensional data on the patient's affected area of the cranial bone is obtained by a computer tomography (CT) and the like, and based on the three-dimensional data, the shape of the cranial bone plate 1 is designed. Based on the shape design, the material for the substrate is processed under a computer control process, so that the cranial bone plate 1 with the desired dimension and shape can be fabricated.
(Cross-Linking Step 1-A: High-Energy Radiation Step)

To enhance the abrasion resistance of the substrate 2, polymer material forming the substrate 2 may be subjected to crosslinking treatment (crosslink treatment: CL). For example, the block-shaped material for the substrate before forming is irradiated with high-energy radiation (e.g., X rays, γ rays, or electron beams), thereby forming crosslinks between the polymer materials (e.g., PE) included in the material for the substrate, thus producing a "crosslinked block-shaped material for the substrate (e.g., including crosslinked polymer material, such as a crosslinked UHM-WPE (CLPE)). The thus-obtained "crosslinked block-shaped material for the substrate" can be cut to thereby provide the substrate 2.

In the crosslinking treatment, the irradiation of the material for the substrate with the high energy radiation generates free radicals within the polymer material included in the material for the substrate. The free radicals forms bonding between molecular chains of the polymer material, which has a mesh structure. The mesh structure enhances a bonding force between the molecular chains in the polymer material, thereby improving its mechanical properties (e.g., abrasion resistance, impact resistance, etc.).

In another example, first, the substrate 2 including the polymer material (e.g., PE) may be provided, and the substrate 2 may be then irradiated with the high-energy radiation, thereby applying the crosslinking treatment to the polymer material.

Like the present invention, in the case of the substrate 2 including the antioxidant, parts of radicals generated in the substrate 2 are trapped in the antioxidant, whereby the crosslinking reaction hardly progresses. For this reason, to make the adequate crosslinking reaction progress within the substrate 2 including the antioxidant, it is necessary to irradiate the substrate with the high-energy radiation at a relatively high dose (for example, of 75 kGy to 200 kGy, and more preferably 100 kGy to 150 kGy). PE not including the antioxidant can make the adequate crosslinking reaction progress by irradiation with high energy radiation of 50 to 100 kGy.

(Cross-Linking Step 1-B: Heat Treatment Step)

After irradiation with the high-energy radiation, the polymer material may be subjected to a heat treatment. The free radicals generated in the polymer material by the high-energy radiation more effectively induce the crosslinking reaction by being subjected to the heat treatment, whereby the crosslinking reaction is promoted. The temperature range for the heat treatment is preferably set in a range of 110 to 130° C., and the processing time for the heat treatment is preferably set in a range of 2 to 12 hours.

As mentioned above, the crosslinking treatment can be performed either before or after the molding process. However, the crosslinking treatment is desirably performed before the molding process for the following reason. The high-energy radiation required for the crosslinking treatment might change the size of the substrate 2 and thus it is not desirable to conduct the crosslinking treatment after the molding process. Further, the crosslinking treatment is desirably performed before "Step 2: step of cleaning a surface 20" for the following reasons.

In the present invention, "Step 3: step of forming a polymer film(s)" is performed after "Step 2: step of cleaning the surface 20". Since the cleaning effect of the surfaces 20 is gradually reduced over time, it is not desirable that another process (for example, crosslinking treatment) is performed between these steps. Further, since the high-energy radiation required for the crosslinking treatment is not preferable to the polymer film(s) 40, it is not also desirable that the crosslinking treatment is performed after "Step 3: step of forming the polymer film(s)". Based on these reasons, the crosslinking treatment is preferably performed before the cleaning step.

Note that the crosslinking treatment of the polymer material can also be performed by adding a crosslinking agent to the material for the substrate. However, the cranial bone plate 1 used in the artificial joint is installed within the living body over a long period of time. It is undesirable to use the crosslinking agent in which safety is not guaranteed.

(Step 2: Step of Cleaning Surface 20)

In this step, at least a part of the surface of the substrate 2 (specifically, the surface 20) is cleaned with a cleaning liquid. This step enables formation of the polymer film(s) 40 with few defects on the surfaces 20 in the next "Step 3: step of forming the polymer film(s) 40".

To form the polymer film(s) 40, polymer chains included in the polymer film(s) 40 are graft-polymerized onto the surfaces 20 of the substrate 2. By the graft polymerization, the polymer chains can be stably fixed to the surface 20 of the substrate 2. The conditions for the graft polymerization can be controlled (for example, to strength the intensity of ultraviolet irradiation, to increase the concentration of a polymerization initiator, to increase the time of ultraviolet irradiation, and the like) to thereby increase the number of polymerization starting points. As a result, a number of graft polymer chains can be formed on the surface 20 of the substrate 2, thereby increasing the density of the polymer film(s).

However, in the presence of the antioxidant onto the surface 20 of the substrate 2, the polymer chains are less likely to be graft-polymerized onto the surface 20. This is because the antioxidant intervenes between a monomer for forming the polymer film(s) 40 and the surface 20, causing the monomer not to approach the surface 20, resulting in failing to make graft polymerization of polymer chains in a region near the surface. Thus, in the region near the surface 20, the polymer film(s) 40 has holes, and/or a gap occurs between the polymer film(s) 40 and the surface 20.

The polymer chains included in the polymer film(s) 40 are formed by a surface-initiated graft polymerization reaction using radicals generated on the superficial part of surface 20. However, some kinds of antioxidants included in the polymer material tend to trap therein the radicals required for the radical polymerization to inactivate them, possibly inhibiting the surface-initiated graft polymerization reaction. This is one of the reasons for generating the hole and gap in the polymer film(s) 40.

Thus, the surfaces 20 are cleaned before forming the polymer film(s) 40, and the antioxidant is removed only from the surfaces 20, so that monomers for forming the polymer film(s) 40 can approach each other across the whole surfaces 20. As a result, the polymer film(s) 40 that has no defects, such as holes or gaps, or few defects can be formed.

As mentioned above, the cleaning step is performed for the purpose of washing out the antioxidant from the surface 20. Thus, the cleaning liquid suitable for use is one that has high cleaning effect of the antioxidant. On the other hand, when using, as the cleaning liquid, an organic solvent that can dissolve the polymer material included in the substrate 2, the superficial part of the surface 20 might be damaged, and thus such an organic solvent is not preferable for use. Further, the organic solvent might decrease the concentration of antioxidant included in the polymer material to reduce the antioxidative properties of the cranial bone plate 1. Thus, the organic solvent is not preferable. Thus, an aqueous solution including a surfactant is preferably used as the cleaning liquid. A lipophilic antioxidant can be removed by the cleaning effect of the surfactant, whereas a hydrophilic antioxidant can be removed with water as a solvent. Furthermore, the aqueous solution including the surfactant has the advantage that it is least likely to damage the substrate 2 comprising an organic material.

In the cleaning step, the substrate is immersed in the cleaning liquid including the surfactant at a cleaning temperature of 40 to 80° C. and preferably 70 to 80° C., for a cleaning time of 6 to 48 hours and preferably 12 to 48 hours. Cleaning under these conditions enables the formation of the polymer film(s) 40 with extremely few defects, such as holes and gaps, when forming the polymer film(s) 40 in the next step. For example, after cleaning the substrate at the cleaning temperature of 70° C. for a cleaning time of 6 hours, the polymer film(s) 40 with few defects can be formed. Note that when the cleaning temperature is lower than 70° C., even the cleaning time is increased to more than 6 hours, so that the same effects can be obtained. When the cleaning temperature is higher than 70° C., the cleaning time is decreased to less than 6 hours, so that the same effects can be obtained.

(Step 3: Step of Forming Polymer Film(s) 40)

In this step, polymer chains comprising a (meth)acrylate compound is fixed by graft polymerization to at least a part (specifically, the surfaces 20) of the surface of the substrate 2 after the cleaning step, whereby the polymer film(s) 40 is formed on the surfaces 20 of the substrate 2.

To produce the cranial bone plate 1 in the present invention, it is necessary to fix the polymer film(s) 40 to the surfaces 20 of the cranial bone plate 1. Although there are several fixing methods in the related art, in the present invention, polymerizable monomers comprising (meth)acrylate compounds are connected on the surfaces 20 by the graft polymerization reaction starting from the superficial part of the surface 20, thereby fixing the polymer film(s) 40. This method has advantages that only the surfaces 20 can be modified without degrading the properties of the polymer material, such as the strength, that forms the cranial bone plate 1, that a connecting part is chemically stable, and further that a large amount of poly(meth)acrylic acid ester is formed on the surfaces 20 of the substrate 2, thereby increasing the density of the polymer film(s) 40.

A specific procedure for forming the polymer film(s) 40 involves irradiating the surfaces 20 with ultraviolet rays with monomers of (meth)acrylate compound in contact with the surfaces 20. An ultraviolet intensity is preferably 0.5 mW/cm$^2$ or more, which enables the formation of the polymer film(s) 40 on the surfaces 20. An irradiation intensity is preferably in a range of 1.0 mW/cm$^2$ to 13.0 mW/cm$^2$, which enables the formation of the polymer film(s) 40 with fewer defects. The irradiation intensity is more preferably in a range of 1.0 mW/cm$^2$ to 9.5 mW/cm$^2$, and particularly preferably in a range of 2.0 mW/cm$^2$ to 9.5 mW/cm$^2$, which enables the formation of the polymer film(s) 40 with much fewer defects. In terms of production efficiency, the irradiation intensity is most preferably in a range of 2.0 mW/cm$^2$ to 5.0 mW/cm$^2$. The irradiation intensity in this range can form the polymer film(s) 40 with very little defect.

An ultraviolet irradiation time is preferably in a range of 0.5 hour to 24 hours, whereby the continuous polymer film(s) 40 can be formed on the surfaces 20 at the ultraviolet irradiation intensity of, e.g., 0.5 mW/cm$^2$ or higher. The irradiation time is more preferably in a range of 0.5 hour to 12 hours, whereby the continuous polymer film(s) 40 can be formed on the surfaces 20 at the ultraviolet irradiation intensity of, e.g., 1.0 mW/cm$^2$ or higher. The irradiation time is further preferably in a range of 0.5 hour to 6 hours, whereby the continuous polymer film(s) 40 can be formed on the surfaces 20 at the ultraviolet irradiation intensity of, e.g., 2.0 mW/cm$^2$ or higher. The irradiation time is particularly preferably in a range of 0.5 hour to 3 hours, whereby the continuous polymer film(s) 40 can be formed on the surfaces 20 at the ultraviolet irradiation intensity of, e.g., 5.0 mW/cm$^2$ or higher. In terms of production efficiency, the irradiation time is preferably 3 hours or less.

When the irradiation intensity of ultraviolet rays to form the polymer film(s) 40 is converted into a total energy (=intensity (mW/cm$^2$)×time (seconds)), the total energy is preferably in a range of 6,000 mJ/cm$^2$ to 70,000 mJ/cm$^2$, so that the continuous polymer film(s) 40 can be formed on the surfaces 20. The total energy is more preferably in a range of 7,000 mJ/cm$^2$ to 50,000 mJ/cm$^2$, so that the polymer film(s) 40 with fewer defects can be formed. The total energy is further preferably in a range of 10,000 mJ/cm$^2$ to 45,000 mJ/cm$^2$, so that the polymer film(s) 40 with fewer defects can be formed on the surfaces 20.

To bring the surfaces 20 into contact with the monomer of (meth)acrylate compound, for example, the surfaces 20 of the cranial bone plate 1 may be immersed in a solution including a polymerizable monomer. The surfaces 20 are irradiated with ultraviolet rays while being immersed in the solution, so that the polymer film(s) 40 can be formed on the surfaces 20.

When the polymer film(s) 40 is formed while being immersed in the solution in this way, not only the surfaces 20 (outer surface 21 and inner surface 22) of the substrate 2, but also the outer peripheral surface 23, the inner side surfaces 26a of the through holes 26, and the inner side surface of the screw holes 27 can be easily covered as a whole with the polymer film(s) 40.

Suitable solutions in the present invention can include water, alcohol, and alcoholic aqueous solutions. The solution suitable for use needs to dissolve or disperse at least a monomer of a (meth)acrylate compound, and is preferably one that hardly erodes or dissolves the substrate.

The concentration of the polymerizable monomer in the solution is preferably in a range of 0.15 mol/L to 1.0 mol/L, so that the formation of the polymer film(s) 40 can be formed on the surface 20. The concentration of the polymerizable monomer in the solution is more preferably in a range of 0.27 mol/L to 1.0 mol/L, so that the continuous polymer film(s) 40 can be formed. The concentration of the polymerizable monomer in the solution is further preferably in a range of 0.27 mol/L to 0.8 mol/L, particularly preferably, in a range of 0.27 mol/L to 0.55 mol/L, so that the polymer film(s) 40 with fewer defects can be continuously formed.

In terms of forming the preferable polymer film(s) 40, the concentration of the polymerizable monomer may exceed 1.0 mol/L. However, in preparing a solution at a concentration exceeding 1.0 mol/L, it is very difficult to dissolve the polymerizable monomer in the solvent. Furthermore, some polymerizable monomers are expensive. The use of the solution including such a polymerizable monomer at a concentration exceeding 1.0 mol/L might lead to an increase in production cost.

Before irradiation of the above-mentioned ultraviolet rays, at least a part of the surface (specifically, the surfaces 20) of the substrate 2 may be coated with a photopolymerization initiator. The photopolymerization initiator is a compound that is irradiated with light having a wavelength required for excitation (for example, ultraviolet rays and the like) at an intensity needed for excitation to thereby be excited to generate radicals. Once the photopolymerization initiator coating the surfaces 20 is irradiated with the ultraviolet rays and the like, first, radicals are generated in the photopolymerization initiator. Subsequently, the generated radicals are moved to the surfaces 20, and the radicals that have moved to the superficial parts of surfaces 20 react with the polymerizable monomers in the solution to start graft polymerization. The polymerizable monomers in the solution are gradually polymerized to form polymer chains. In this way, an aggregation of these polymer chains covering the surfaces 20 forms the polymer film(s) 40.

Taking into consideration the growth process of such polymer chains, the thickness of the polymer film(s) 40 is supposed to be affected by the concentration of the polymerizable monomers in the solution.

In the growth process of the polymer chains, once the polymerizable monomer in the solution comes into contact with a radical located at the end of the polymer chain, the radical attacks the polymerizable monomer, causing the polymerization to progress forward. To grow the polymer chains longer, the probability of contact needs to be enhanced such that the polymerizable monomer is in contact with the radical before a termination reaction of the radical.

The concentration of the polymerizable monomers in the solution and the temperature of the solution are considered to affect the probability of contact between the polymerizable monomers and the radicals. For example, if the polymerizable monomer concentration is too low, the probability that the polymerizable monomers come across the radicals will become lower, whereby the number of radicals inactivated before contact with the polymerizable monomers would be increased. If the temperature of the solution is too low, the motility of the monomers in the solution will be reduced, decreasing the probability that the radicals meet the polymerizable monomers, whereby the number of radicals inactivated before contact with the polymerizable monomers would be increased. As a result, the polymer chains that are short in length (that is, thin polymer film(s) 40) will be formed. This results in the short polymer chains (that is, thin polymer film(s) 40). For this reason, a polymerizable monomer solution having a certain concentration or more, at a given temperature or higher should be used in order to form the long polymer chains (that is, to make the polymer film(s) 40 thicker).

Appropriate concentration of the polymerizable monomer solution varies depending on other polymerization conditions, but may be, for example, 0.15 mol/L or more. An appropriate temperature of the polymerizable monomer solution also varies depending on other polymerization conditions, but may be, for example, 40° C. or higher.

The density of the obtained polymer film(s) 40 changes depending on the intensity and irradiation time of ultraviolet rays.

After the polymer film(s) formation step, a sterilization treatment by irradiation with γ rays is preferably performed. For example, the sterilization treatment can be performed with γ rays at 25 kGy to 75 kGy.

The prosthetic member 1 of the present invention and materials suitable for use in a production method therefor will be described in detail below.

(Substrate 2)

The substrate 2 of the prosthetic member 1 is formed of materials for the substrate including the polymer material and antioxidant.

(Polymer Material)

For example, a PE-based material can be used as polymer material included in the substrate 2. The PE-based material has a double bond in its molecule, which differs from other polymer materials (polymethyl methacrylate, polyether ether ketone) usable in the prosthetic member. Thus, when the PE-based material is irradiated with high-energy radiation, the double bond can be cut to generate radicals, thereby generating intermolecular crosslinking.

Among the PE-based materials, particularly, an ultrahigh molecular weight polyethylene (UHMWPE) is preferably used. The UHMWPE are suitable for use in the substrate 2 because of its excellent mechanical properties, including abrasion resistance, deformation resistance, and the like, in the PE-based materials. The UHMWPE has higher abrasion resistance as its molecular weight increases. Thus, the UHMWPE suitable for use has at least a molecular weight of $1\times10^6$ g/mol (1,000,000 g/mol) or more, preferably, a molecular weight of $3\times10^6$ g/mol (3,000,000 g/mol) or more, and more preferably, in a range of $3\times10^6$ g/mol (3,000,000 g/mol) to $7\times10^6$ g/mol (7,000,000 g/mol), and particularly, preferably $3\times10^6$ g/mol (3,000,000 g/mol) to $4\times10^6$ g/mol (4,000,000 g/mol).

Here, the molecular weight of the UHMWPE included in the substrate is determined based on the formula (1) below by measuring the viscosity of a decahydronaphthalene (decalin) solution at 135° C.

[Equation 1]

$$\text{Molecular Weight}=5.37\times10^4\times(\text{Intrinsic Viscosity})^{1.49} \quad (1)$$

In particular, in the use as the prosthetic member, such as a cranial bone plate 1, the non-crosslinked UHMWPE is more appropriate because of its excellent mechanical properties (regarding, e.g., the impact resistance, the tensile strength, and the like) than a crosslinked polyethylene (crosslink polyethylene: CLPE) obtained by crosslinking of UHMWPE. On the other hand, in the use as a sliding member, CLPE is more appropriate because of its excellent abrasion resistance than the non-crosslinked UHMWPE.

(Antioxidant)

As an antioxidant included in the substrate 2, an antioxidant having a phenolic hydroxyl group or tocotrienol group can be used. Specifically, suitable antioxidants for use can include hindered amine-based antioxidants, hindered phenol antioxidants, phosphorus-based antioxidants, sulfur-based antioxidants, and lipid-soluble vitamin E group (tocopherols).

Examples of the hindered amine-based antioxidant include 1,2,2,6,6-penta methylpiperidinyl methacrylate, 2,2,6,6-tetramethylpiperidinyl methacrylate, bis(2,2,6,6-tetramethyl-4-piperidine)sebacate, polymer of dimethyl succinate and 4-hydroxy-2,2,6,6-tetramethyl-1-piperidine ethanol, N,N',N''',N'''-tetrakis-(4,6-bis-(butyl-(N-methyl-2,2,6,6-tetramethylpiperidin-4-yl)amino)-triazin-2-yl)-4,7-diazadecane-1,10-diamine, decanedioic acid bis(2,2,6,6-tetramethyl-1-(octyloxy)-4-piperidinyl)ester, bis(1,2,2,6,6-pentamethyl-4-piperidyl) [[3,5-bis(1,1-dimethylethyl)-4-hydroxyphenyl]methyl]butylmalonate, a reaction product of cyclohexane and peroxide N-butyl-2,2,6,6-tetramethyl-4-piperidineamine-2,4,6-trichloro-1,3,5-triazine, reaction product of cyclohexane and 2-aminoethanol and, bis(1,2,2,6,6-pentamethyl-4-piperidyl)sebacate, methyl-1,2,2,6,6-pentamethyl-4-piperidyl sebacate, and tetrakis(1,2,2,6,6-pentamethyl-4-piperidine)-1,2,3,4-butane tetracarboxylate.

Examples of the hindered phenol-based antioxidant include
2-t-butyl-4-methoxyphenol, 3-t-butyl-4-methoxyphenol, 2,6-di-t-butyl-4-ethylphenol,
2,2'-methylene-bis(4-methyl-6-t-butylphenol),
4,4'-thiobis-(3-methyl-6-t-butylphenol),
4,4'-butylidene bis(3-methyl-6-t-butylphenol),
1,1,3-tris(2-methyl-4-hydroxy-5-t-butylphenyl)butane,
1,3,5-trimethyl-2,4,6-tris(3,5-di-t-butyl-4-hydroxybenzyl) benzene, and
tetrakis-[methylene-3-(3',5'-di-t-butyl-4'-hydroxyphenyl) propionate]methane.

Examples of the phosphorus-based antioxidant include triphenyl phosphite, diphenyl isodecyl phosphite, phenyl diisodecyl phosphite, 4,4'-butylidene-bis(3-methyl-6-t-butylphenyl ditridecyl)phosphite, cyclic neopentanetetrayl bis(dinonylphenyl)phosphite, cyclic neopentanetetrayl bis(dinonylphenyl)phosphite, cyclic neopentanetetrayl tris(nonylphenyl)phosphite, cyclic neopentanetetrayl tris(dinonylphenyl)phosphite, 10-(2,5-dihydroxyphenyl)-10H-9-oxa-10-phosphaphenanthrene-10-oxide, diisodecyl pentaerythritol diphosphite, and tris(2,4-di-t-butylphenyl) phosphite.

Examples of the sulfur-based anti-oxidant include dilauryl 3,3'-thiodipropionate, distearyl 3,3'-thiodipropionate, N-cyclohexylthiophthalimide, and N-n-butylbenzenesulfonamide.

Examples of the lipid-soluble vitamin E group (tocopherols) as the antioxidant include tocopherols, tocotrienols, and derivatives thereof, specifically, tocopherols and derivatives thereof, such as α-tocopherol, β-tocopherol, γ-tocopherol, δ-tocopherol, dl-σ-tocopherol, dl-β-tocopherol, dl-γ-tocopherol, dl-δ-tocopherol, dl-α-tocopherol acetate, dl-α-tocopherol nicotinate, dl-α-tocopherol linoleate, dl-α-tocopherol succinate, and tocotrienols and derivatives thereof, such as α-tocotrienol, β-tocotrienol, γ-tocotrienol, and δ-tocotrienol. These elements may be used alone or in combination. However, the use of them in combination is preferable, specifically, examples of a mixture can include those called extracted tocopherol, mixed tocopherol, and the like.

Among these antioxidants, the vitamin E has high safety and barely adversely affects the brain 90. Thus, the vitamin E is preferably used in the prosthetic member used in the living body.

In addition to the antioxidants discussed above, vitamins such as vitamin A and vitamin C, aromatic amines, amines having an aldehyde group or ketone group, salts of an aminophenol and their condensates can also be used as the antioxidant. The antioxidant that is less likely to be dissolved in squalene is more preferable because it can exhibit the effect of further suppressing the absorption and diffusion of squalene in use.

The content of the antioxidant is preferably in a range of 0.01 to 5% by weight in the polymer material forming the substrate 2 in terms of the effect of antioxidation, more preferably in a range of 0.05 to 0.7% by weight, and particularly preferably in a range of 0.05 to 0.15% by weight.

The antioxidant can eliminate radicals generated in the crosslinking reaction of the substrate 2. However, the content of the antioxidant is set in a range of 0.01 to 5% by weight, promoting the crosslinking reaction to thereby produce the substrate 2 including CLPE.

(Polymer Film(s) 40)

In forming the polymer film(s) 40, polymerizable monomers comprising a (meth)acrylate compound are used. In particular, the monomer is selected that is poorly-oluble, very poorly-soluble, or insoluble in squalene and has a functional group graft-polymerizable with the polymer material forming the substrate 2, whereby the polymer film(s) 40 can be graft-polymerized onto the surface 20 of the cranial bone plate 1. The (meth)acrylate compound is preferably a (meth) acrylate ester.

Suitable (meth)acrylate compounds in the present invention include, for example, (meth)acrylic acid; alkyl (meth)acrylates such as methyl (meth)acrylate, ethyl (meth)acrylate, n-propyl (meth)acrylate, isopropyl (meth)acrylate, n-butyl (meth)acrylate, isobutyl (meth)acrylate, tert-butyl (meth)acrylate, n-pentyl (meth)acrylate, n-hexyl (meth)acrylate, cyclohexyl (meth)acrylate, n-heptyl (meth)acrylate, n-octyl (meth)acrylate, 2-ethylhexyl (meth)acrylate, nonyl (meth)acrylate, decyl (meth)acrylate, dodecyl (meth)acrylate, and stearyl (meth)acrylate; phenyl (meth)acrylate, toluyl (meth)acrylate, and benzyl (meth)acrylate; (meth)acrylic acid alkoxy esters such as 2-methoxyethyl (meth)acrylate, and 3-methoxybutyl (meth)acrylate; hydroxylalkyl (meth)acrylates such as hydroxyethyl (meth)acrylate, 2-hydroxylethyl (meth)acrylate, and 2-hydroxypropyl (meth)acrylate; glycidyl (meth)acrylates; (meth)acrylic acid esters including a silane compound, such as 2-aminoethyl (meth)acrylate and γ-(methacryloyloxypropyl)trimethoxysilane; ethylene oxide adducts of (meth)acrylic acids; fluorine-group including (meth)acrylic acid esters such as trifluoromethyl methyl (meth)acrylate, 2-trifluoromethylethyl (meth)acrylate, 2-perfluoroethylethyl (meth)acrylate, 2-perfluoroethyl-2-perfluorobuthylethyl (meth)acrylate, 2-perfluoroethyl (meth)acrylate, perfluoromethyl (meth)acrylate, diperfluoromethylmethyl (meth)acrylate, 2-perfluoromethyl-2-perfluoroethylmethyl (meth)acrylate, 2-perfluorohexylethyl (meth)acrylate, 2-perfluorodecylethyl (meth)acrylate, and 2-perfluorohexadecylethyl (meth)acrylate; 2-(phosphonooxy)ethyl methacrylates; and (meth)acrylate compounds including oligo ethylene glycol, such as methoxy oligoethylene glycol methacrylate.

The polymer film(s) 40 may be a film comprising a polymer formed from one kind of (meth)acrylate compound, or of a copolymer formed from two or more kinds of (meth)acrylate compounds.

An MPC monomer has a chemical structural formula to be described below, which includes a phosphorylcholine group and a polymerizable methacrylic acid unit. The MPC monomer is characterized by that a MPC polymer having a high molecular weight can be easily formed by radical polymerization (Ishihara et al.: Polymer Journal vol. 22, pp. 355 (1990)). Thus, when the polymer film(s) 40 is intended to be synthesized from the MPC monomer, the graft-polymerization between the polymer film(s) 40 and the surfaces 20 can be conducted under relatively moderate conditions, so that the polymer film(s) 40 having a high density can be formed, thereby forming, on the surface 20, polymer chains of (meth)acrylate ester that is insoluble even in a large amount of squalene.

[Chemical formula 1]

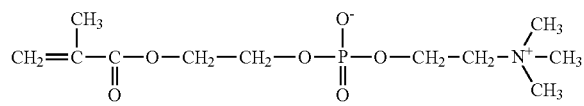

The polymer film(s) 40 suitable for use in the present invention can be formed not only by a polymer configured of one or two or more kinds of (meth)acrylate compound monomers, but also by a copolymer. The copolymer includes one or two or more of (meth)acrylate compound monomers mentioned above, as well as a monomer having functions of adequate infection resistance, antithrombogenicity, and/or good binding properties or the like with bones (e.g., a butyl methacrylate monomer, a trimethoxysilyl propyl methacrylate monomer, etc.). In this way, the functions of improving infection resistance, antithrombogenicity, binding properties with bones, and the like can be imparted to the polymer film(s) 40.

(Cleaning Liquid)

The cleaning liquid used in the production method of the present invention may include an organic solvent and/or water. In particular, the cleaning liquid is preferably obtained by dissolving a surfactant in water. A lipophilic one (e.g., vitamin E group) of the antioxidants can be easily removed by the aqueous solution including the surfactants.

The surfactant may be selected according to the antioxidant to be removed as appropriate. Any one of a cationic surfactant, an anionic surfactant, non-ionic surfactant, and ampholytic surfactant can be used. When using vitamin E group as the antioxidant, the non-ionic surfactant is preferable.

Examples of the surfactant include non-ionic surfactants, cationic surfactants, anionic surfactants, and ampholytic surfactants. In particular, the non-ionic surfactant is preferably used.

The non-ionic surfactant is preferably a polyoxyethylene-based surfactant having a HLB value of 10 to 18 (particularly, HLB value of 13 to 18). Examples of polyoxyethylene-based surfactants suitable for use include polyoxyethylene alkyl ethers, polyoxyethylene sorbitan fatty acid esters (Tween20 (registered trademark)), polyoxyethylene octylphenyl ether (e.g., polyoxyethylene p-t-octyl phenyl ether), and polyoxyethylene nonylphenyl ether (e.g., polyoxyethylene p-t-nonylphenyl ether). Tween 20 (registered trademark) is suitable for use as the surfactant applied to the cleaning liquid because it is one of food additives and has high safety to human body.

The non-ion surfactant can be used independently, or alternatively two or more kinds of the non-ion surfactants can be mixed in use. The concentration of the non-ion surfactant may be any value that can remove the antioxidant on the surface of the substrate, but preferably in a range of 0.01 to 10.0% by weight, more preferably in a range of 0.1 to 5.0% by weight, further preferably in a range of 0.1 to 1.0% by weight, and particularly preferably in a range of 0.3 to 1.0% by weight.

(Light Source for Ultraviolet Irradiation)

Various light sources can be used as the light source for irradiation of ultraviolet rays (having a wavelength, for example, of 300 to 400 nm). For example, a high-pressure mercury lamp (UVL-400HA, produced by RIKOH KAGAKU Co., Ltd.), a LED (MeV365-P601JMM, produced by Yen Electron Volt. Co. Ltd.) and the like can be used.

(High-Energy Radiation Source for Cross-Linking Treatment)

Various radiation sources can be used as a high-energy radiation source used for crosslinking treatment. For example, a radiation device can be used which employs Co (Cobalt) 60 as a γ radiation source, while an accelerator for discharging the electron beam is used as an electron beam source.

Second Embodiment

The present invention is directed to a prosthetic member implanted into the living body for a long time, and can be generally applied to any prosthetic member that utilizes a polymer material for the substrate. This embodiment will describe an example of the prosthetic member to which the present invention can be applied.

(Artificial Joint)

Figure 4:
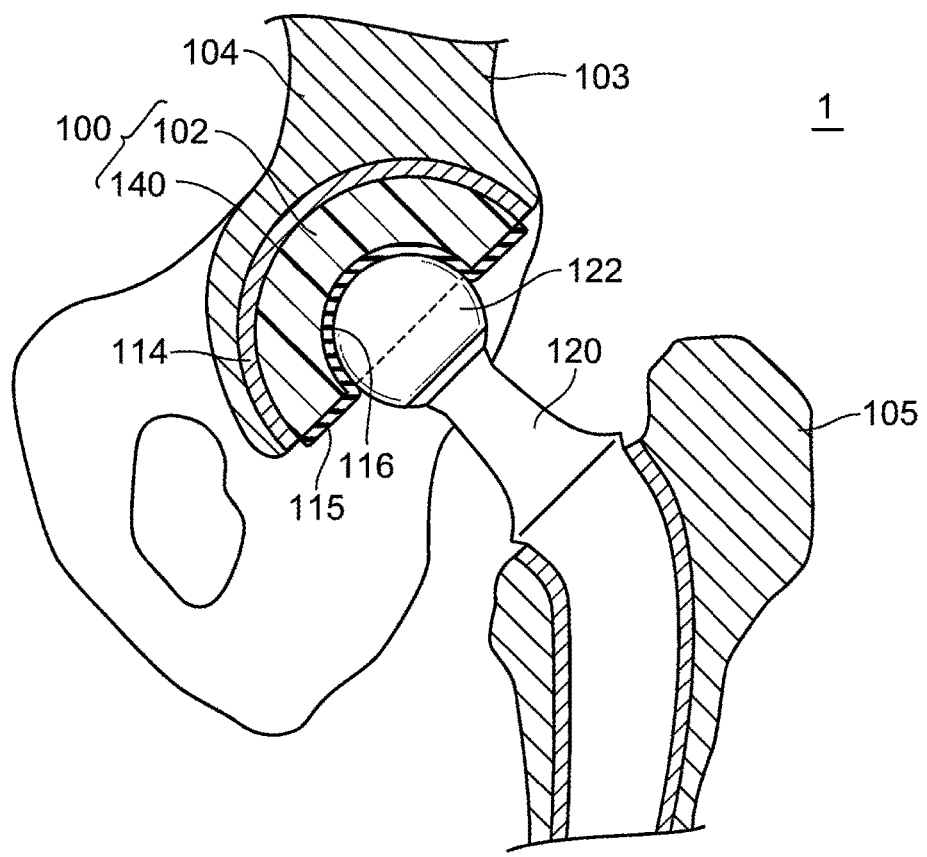
FIG. 4 is a partial cross-sectional view of an artificial hip joint according to a second embodiment.

An artificial hip joint shown in FIG. 4 includes an acetabular cup 100 fixed to an acetabulum 104 of a hip bone 103, and a femoral stem 120 fixed to a femur 105. The prosthetic member of the present invention can be used in the acetabular cup 100. The acetabular cup 100 includes a substrate 102 including the polymer material and antioxidant, and a polymer film(s) 140 covering the surface of the substrate 102. The polymer film(s) 140 should cover at least an area of the surface of the acetabular cup 100 where oxidation tends to occur (specifically, an area of the surface where the polymer film(s) 140 comes into contact with a biological fluid after fixing the acetabular cup 100 to the acetabulum 104), thereby suppressing the immersion of lipid, such as squalene. Specifically, an inner surface 116 of the acetabular cup 100 (surface along which an epiphysis 122 of the femoral stem 120 slides) and end surfaces 115 thereof are in contact with the biological fluid and thus are preferably configured to be covered by the polymer film(s) 40. Note that after fixing the acetabular cup 100 to the acetabulum 104, an outer surface 114 of the acetabular cup 100 hardly comes into contact with the biological fluid and thus does not need to be provided with the polymer film(s) 140.

The prosthetic member of the present invention can be used as a sliding member and the like included in artificial Joints, which includes, in addition to the artificial hip joint, artificial shoulder joint, artificial elbow joint, artificial knee joint, artificial ankle joint, and artificial finger joint.

Example 1

(Measurement of Squalene Index)

To examine the adsorption or absorption of squalene in the prosthetic member 1 in the present application, rectangular samples (i) to (iv) were prepared. Manufacturing conditions for the respective samples are as shown below.

Sample (i): Crosslinked Polyethylene Sample (CLPE)

UHMWPE powder having a molecular weight of approximately 3.5 million was compaction molded. The compaction-molded body obtained in this way was irradiated with γ rays at a dose of 50 kGy, and then subjected to heat treatment at 123° C. for 12 hours, whereby PE was crosslinked to produce a CLPE. A rectangular sample block (10 mm length×6 mm width×20 mm height) was cut out of the thus-obtained CLPE, and finally, the sample was sterilized by irradiation with γ rays at a dose of 25 kGy under nitrogen atmosphere, thereby producing a sample (i).

Sample (ii): CLPE Sample Coating with a Polymer Film(s) (PMPC-Graft CLPE)

UHMWPE powder having a molecular weight of approximately 3.5 million was compaction molded. The compaction-molded body obtained in this way was irradiated with γ rays at a dose of 50 kGy, and then subjected to heat treatment at 123° C. for 12 hours, whereby PE was crosslinked to produce a CLPE. A rectangular sample block (10 mm length×6 mm width×20 mm height) was cut out of the thus-obtained CLPE.

The obtained CLPE sample block was immersed in a cleaning liquid (a Tween20 (registered trademark) aqueous solution having a concentration of 1.0% by weight) and then cleaned for 12 hours while being stirred. Here, a cleaning temperature was 70° C. After such a cleaning process, the CLPE sample block was immersed in an acetone solution (at a concentration of 10 mg/mL) of benzophenone (photopolymerization initiator) for 30 seconds, and then pulled up quickly to thereby remove the solvent from the surface of the CLPE sample block. The CLPE sample block was immersed in a MPC aqueous solution (at a concentration of 0.5 mol/L and at a temperature of an aqueous solution of 60° C.). Then, the surface of the CLPE sample block was irradiated with ultraviolet rays (at a wavelength of 300 to 400 nm) at an intensity of 5.0 mW/cm$^2$ for 90 minutes (1.5 hours). In this way, the polymer film(s) (MPC polymer film(s)) 40 was formed to be graft-polymerized onto the surface of the CLPE sample block, and finally, the block was sterilized by irradiation with γ rays at a dose of 25 kGy under the nitrogen atmosphere, thereby producing a sample (ii).

Sample (iii): Antioxidant-Included Crosslinked Polyethylene Sample (HD-CLPE)

UHMWPE powder having a molecular weight of approximately 3.5 million and an antioxidant (vitamin E: α-tocopherol) liquid were mixed to prepare mixed powder. The content of vitamin E was 0.1% by mass in UHMWPE. The mixed powder was compaction molded. The compaction-molded body obtained in this way was irradiated with γ rays at a dose of 100 kGy, and then subjected to heat treatment at 123° C. for 12 hours, whereby PE was crosslinked. Note that the vitamin E has the property to eliminate radicals for starting the crosslinking reaction. Thus, the UHMWPE including the vitamin E is less likely to cause the crosslinking reaction, compared to UHMWPE not including vitamin E. The irradiation dose of γ rays on each of the samples (iii) and (iv) was set twice as high as that on each of the samples (i) and (ii). Note that the term "HD-CLPE" as used herein means a (high-dosed) CLPE that is crosslinked by increasing the irradiation dose. A sample block having a rectangular parallelepiped (10 mm length×6 mm width×20 mm height) was cut out of the thus-obtained HD-CLPE, and finally, the sample was sterilized by irradiation with γ rays at a dose of 25 kGy under nitrogen atmosphere, thereby producing a sample (iii).

Sample (iv): Antioxidant CLPE Sample Coated with Polymer Film(s) (PMPC-Graft HD-CLPE)

UHMWPE powder having a molecular weight of approximately 3.5 million and an antioxidant (vitamin E: α-tocopherol) liquid were mixed to prepare mixed powder. The content of vitamin E was 0.1% by mass in UHMWPE. The mixed powder was compaction molded. The compaction-molded body obtained in this way was irradiated with γ rays at a dose of 100 kGy, and then subjected to heat treatment at 123° C. for 12 hours, whereby PE was crosslinked to produce a HD-CLPE. A sample block having a rectangular parallelepiped (10 mm length×6 mm width×20 mm height) was cut out of the thus-obtained HD-CLPE. The obtained HD-CLPE disk was immersed in a cleaning liquid (a Tween20 (registered trademark) aqueous solution having a concentration of 1.0% by weight) and then cleaned for 12 hours while being stirred. Here, a cleaning temperature was 70° C. After such a cleaning process, the CLPE sample block was immersed in an acetone solution (at a concentration of 10 mg/mL) of benzophenone (photopolymerization initiator) for 30 seconds, and then pulled up quickly to thereby remove the solvent from the surface of the HD-CLPE sample block. The HD-CLPE sample block was immersed in a MPC aqueous solution (at a concentration of 0.5 mol/L and at a temperature of an aqueous solution of 60° C.). Then, the surface of the HD-CLPE sample block was irradiated with ultraviolet rays (having a wavelength of 300 to 400 nm) at an intensity of 5.0 mW/cm$^2$ for 90 minutes (1.5 hours). In this way, the polymer film(s) (MPC polymer film(s)) 40 was formed to be graft-polymerized onto the surface of the HD-CLPE sample block, and finally, the block was sterilized by irradiation with γ rays at a dose of 25 kGy under the nitrogen atmosphere, thereby producing a sample (iv).

Referring to a document by Oral et al. (Ebru Oral et al., "A new mechanism of oxidation in ultrahigh molecular weight polyethylene caused by squalene absorption", Journal of Biomedical Materials Research Part B: Applied Biomaterials 100 (2012) p. 742-751), a plurality of pieces of the respective samples (i) to (iv) was prepared and immersed in a squalene solution. Then, the amount of squalene adsorbed at the surface of each sample or absorbed from the surface of each sample was evaluated as a squalene index.

Figure 5A:
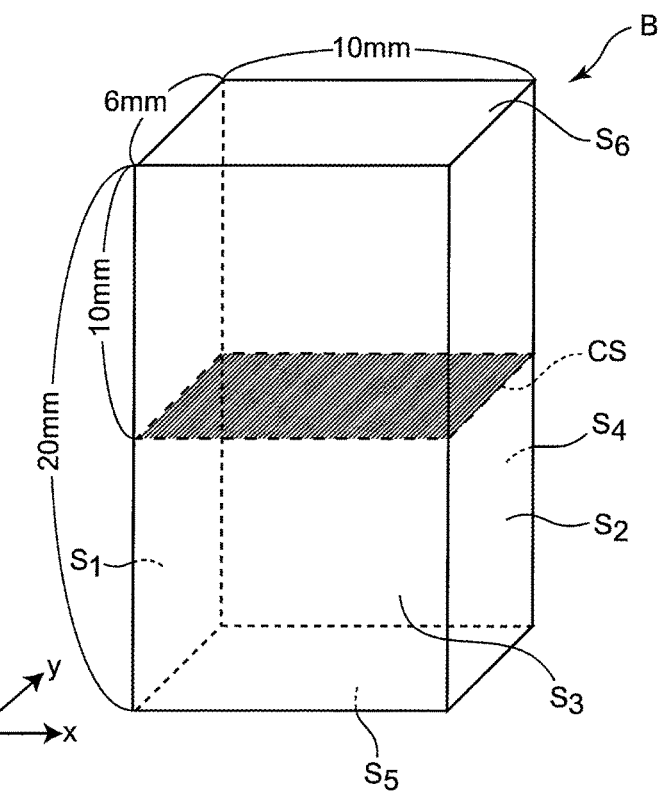
Figure 5B:
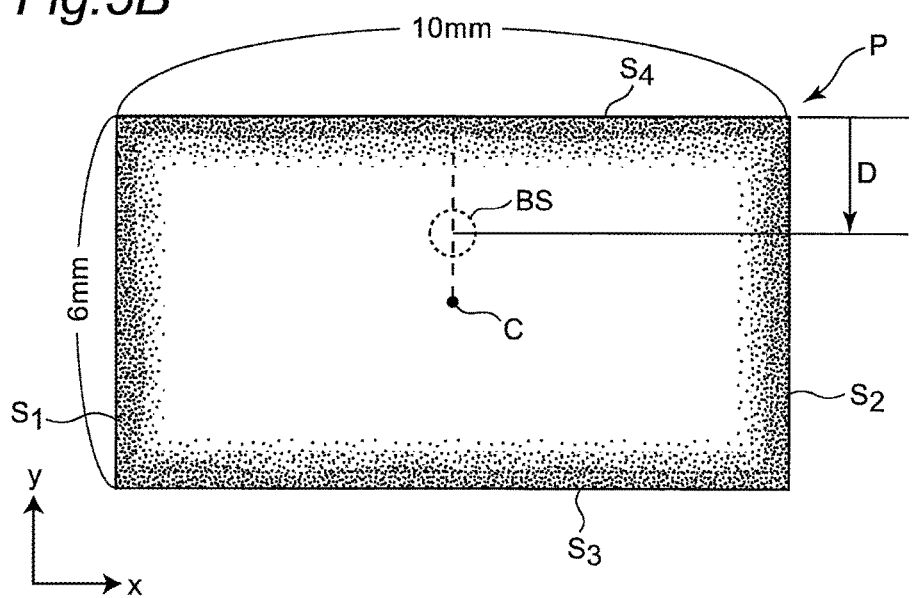

First, each sample was immersed in water for 1.0 hour and subsequently in a squalene solution at a concentration of 100% (at a liquid temperature of 120° C.) for 2.0 hours. Each sample block B immersed in squalene was cut in the intermediate position in the height direction (in the z direction) (at a distance of about 10 mm from an upper surface $S_6$ of the sample block B) on its surface (xy plane) perpendicular to the z direction (see FIG. 5A). Further, the sample block was cut again on the xy plane in the position moved in the Z direction at a distance of only 200 μm from the cross section CS previous cut. In this way, a film-like sample piece P (10 mm length×6 mm width×200 μm thickness) was cut and prepared as a sample for measurement of squalene index (FIG. 5B). This sample piece P was cut from the substantially center of the dimension (height) in the z direction, and thus was not affected by squalene absorbed in the sample from the lower surface $S_5$ and the upper surface $S_6$. On the other hand, four sides of the rectangular sample piece P correspond to four side surfaces $S_1$ to $S_4$ of the state of the sample block B. The squalene absorbed from the four side surfaces $S_1$ to $S_4$ into each sample remains in the sample piece P as squalene absorbed from the four sides of the sample piece P into the center c.

Each sample piece P was measured by using a transmission microscopic Fourier infrared spectroscopy (FT-IR) analysis. The measurement was performed by the transmission method using a microscopic FT-IR analyzer (spectrum one spotlight 300) produced by Perkin Elmer Co., Ltd. at a resolving power of 4 cm$^{-1}$ with the number of runs of 100 runs and wavenumber of 800 to 4,000 cm$^{-1}$. A beam diameter of a beam spot BS of an infrared ray in measurement was approximately 100 μm (about 0.1 mm). The FTIR measurement was performed while changing the distance D between the long side of the rectangular sample piece P ($S_4$ shown in FIG. 5B) and the center of the beam spot BS (the distance D corresponding to an immersion depth of squalene in the sample block B) along a straight line (indicated by a dashed line in FIG. 5B) connecting the central point of the long side of the sample piece P and the center c of the sample piece P. The measurement was conducted at the distances (depths) D=0.05 mm, 0.1 mm, 0.3 mm, 0.5 mm, 1.0 mm, and 3.0 mm. Note that "D=0.05 mm" means the outer edge of the beam spot BS was aligned with the long side of the sample piece and corresponds to the "surface" of the present invention.

Figure 6:
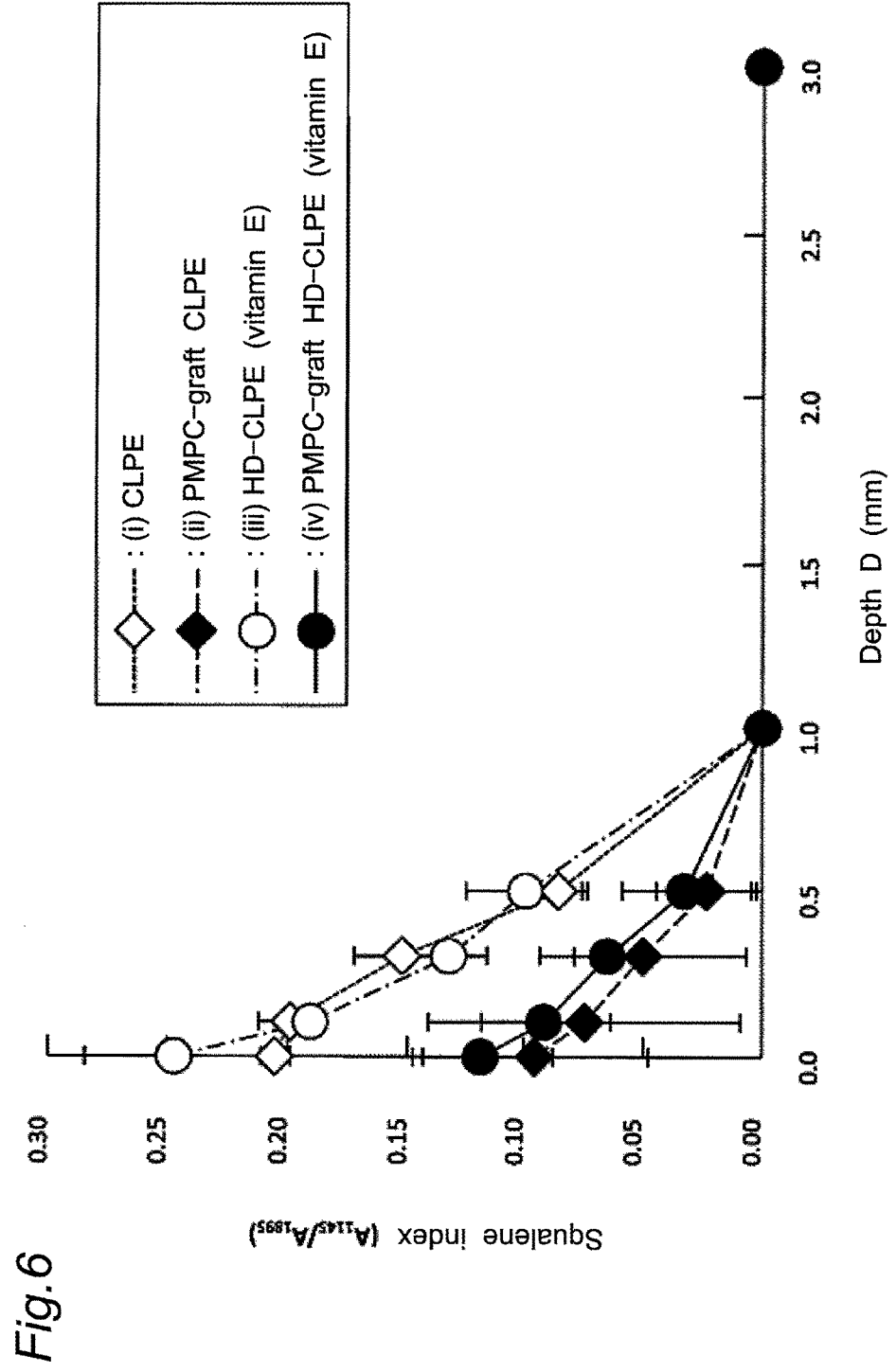
FIG. 6 is a graph showing a squalene index calculated from the results of the FTIR measurement in Example 1.

From the obtained FT-IR spectrum, an area $A_{1895}$ of a peak (near 1895 cm-1) belonging to PE and an area $A_{1145}$ of a peak (near 1145 cm-1) generated by adsorption or absorption of squalene were determined, whereby a relative squalene index ($A_{1145}/A_{1895}$) was calculated from the ratio between these areas. The measurement results are shown in FIG. 6. Note that at the distance (depth) D=0.05 mm, the measurement results were plotted at the position of D=0 in terms of drawing the graph. Unless otherwise specified, the "depth D=0 mm" and "surface" hereinafter mean the "distance D=0.05 mm" in FIG. 5B.

The samples (i) and (iii) not covered with the polymer film(s) 40 showed substantially the same graphs, in which squalene was absorbed from the surface of the substrate 2 to D=1.0 mm. Note that since the graphs of the samples (i) and (iii) were similar to those shown in the document by Oral et al. (that of the sample of CLPE without having a polymer film(s)), they are found to be reasonable results.

In the samples (ii) and (iv) covered with the polymer film(s) 40, squalene was absorbed in the depth of D=1.0 mm from the surface of the substrate 2.

The squalene absorption amount is proportional to the integral of the graph (that is, an area enclosed by the x axis, the γ axis, and the graph). By comparison between the integrals, squalene absorption amounts of the samples (i) and (iii) not covered with the polymer film(s) 40 were found to be appropriately twice as much as that of the samples (ii) and (iv) covered with the polymer film(s) 40.

Figure 7:
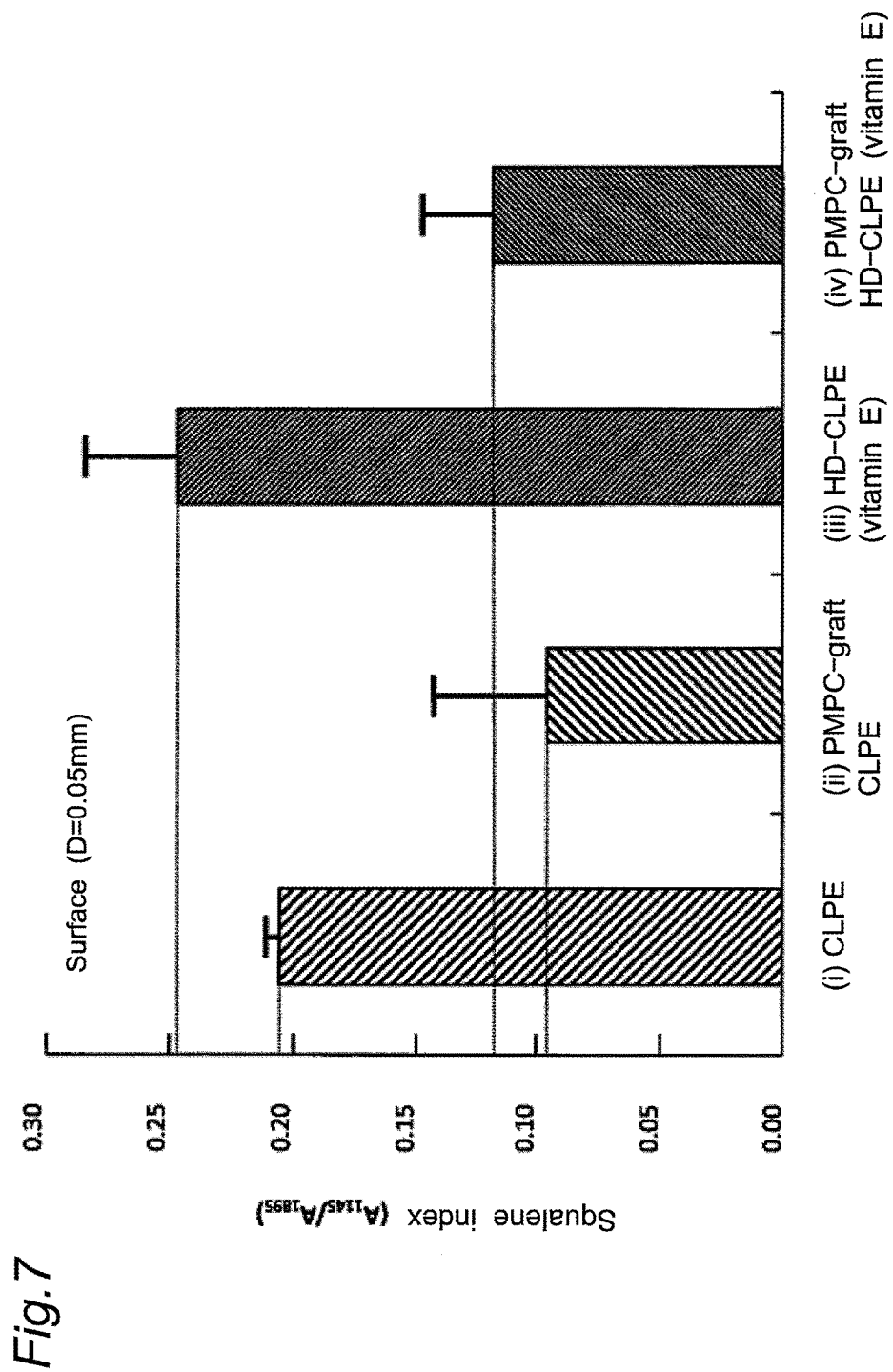
FIG. 7 is a bar graph showing a squalene index calculated from the results of the FTIR measurement in Example 1.

The squalene index at the surfaces of the respective samples (i) to (iv) were shown in FIG. 7. The squalene index of the surface of the sample (i) was 0.21, and that of the sample (iii) was 0.245, which were high. Meanwhile, squalene index of the surface of the sample (ii) was 0.095, and that of the sample (iii) was 0.12, which were low. As can be obvious from the result, squalene index of each of the samples (i) and (iii) not covered with the polymer film(s) 40 was 0.2 or more, which was substantially at the same level as squalene index (of about 0.20 to 0.25) of the surface of the CLPE sample without the polymer film(s) as mentioned in the document by Oral et al. In contrast, squalene index of each of the samples (ii) and (iv) covered with the polymer film(s) was about 0.1, which showed that by covering with the polymer film(s), squalene absorption could be reduced to about a half.

Note that squalene index of the sample (iii) including the vitamin E (antioxidant) was about 0.25, while squalene index of the sample (i) not including the vitamin E was about 0.2. That is, the sample including the vitamin E had squalene index that was about 1.3 times as high as that of the sample not including the vitamin E. It is supposed that since the vitamin E was soluble in squalene, the vitamin E was positively replaced by squalene when being immersed in a squalene solution.

The result of Example 1 showed that coating with the polymer film(s) 40 drastically improved resistance to absorption of squalene (anti-absorption of squalene) in the sample. Particularly, in the sample including the antioxidant, such as the vitamin E, the surface 20 of the substrate 2 is covered with the polymer film(s) 40, which can suppress the reduction in antioxidative properties even under an environment in contact with squalene.

Example 2

(Measurement of Oxidative-Induction Time)

To examine the antioxidative properties of the prosthetic member 1 in the present application, disk-like samples (i) to (iv) were prepared. Production conditions for the respective samples are as shown below.

Sample (i): Crosslinked Polyethylene Sample (CLPE)

UHMWPE powder having a molecular weight of approximately 3.5 million was compaction molded. The compaction-molded body obtained in this way was irradiated with γ rays at a dose of 50 kGy, and then subjected to heat treatment at 123° C. for 12 hours, whereby PE was crosslinked. A disk-shaped sample piece (of 2.5 mm in diameter and 1.0 mm in thickness) was cut out of the thus-obtained CLPE and finally sterilized by irradiation with γ rays at a dose of 25 kGy under the nitrogen atmosphere, thereby producing the sample (i).

Sample (ii): CLPE Sample Coated with Polymer Film(s) (PMPC-Graft CLPE)

UHMWPE powder having a molecular weight of approximately 3.5 million was compaction molded. The compaction-molded body obtained in this way was irradiated with γ rays at a dose of 50 kGy, and then subjected to heat treatment at 123° C. for 12 hours, whereby PE was crosslinked. Then, a sample piece was cut in a disk shape (of 2.5 mm in diameter and 1.0 mm in thickness) from a CLPE obtained by crosslinking PE. The obtained CLPE disk was immersed in a cleaning liquid (a Tween20 (registered trademark) aqueous solution having a concentration of 1.0% by weight) and then cleaned for 12 hours while being stirred. Here, a cleaning temperature was 70° C. After such a cleaning process, the CLPE disk was immersed in an acetone solution (at a concentration of 10 mg/mL) of benzophenone (photopolymerization initiator) for 30 seconds, and then pulled up quickly to thereby remove the solvent from the surface of the CLPE disk. While the CLPE disk was immersed in a MPC aqueous solution (at a concentration of 0.5 mol/L and at a temperature of an aqueous solution of 60° C.), the surface of the CLPE disk was irradiated with ultraviolet rays at an intensity of 5.0 mW/cm$^2$ (with a wavelength of 300 to 400 nm) for 90 minutes (1.5 hours). In this way, the polymer film(s) (MPC polymer film(s)) 40 was formed to be graft-polymerized onto the surface of the CLPE disk, and finally, was sterilized by irradiation with γ rays at a dose of 25 kGy under the nitrogen atmosphere, thereby producing the sample (ii).

Sample (iii): Antioxidant-Included Crosslinked Polyethylene Sample (HD-CLPE)

UHMWPE powder having a molecular weight of approximately 3.5 million and an antioxidant (vitamin E: α-tocopherol) liquid were mixed to prepare mixed powder. The content of vitamin E was 0.1% by mass in UHMWPE. The mixed powder was compaction molded. The compaction-molded body obtained in this way was irradiated with γ rays at a dose of 100 kGy, and then subjected to heat treatment at 123° C. for 12 hours, whereby PE was crosslinked. A disk-shaped sample piece (of 2.5 mm in diameter and 1.0 mm in thickness) was cut from the obtained HD-CLPE and finally sterilized by irradiation with γ rays at a dose of 25 kGy under the nitrogen atmosphere, thereby producing the sample (iii).

Sample (iv): Antioxidant CLPE Sample Coated with Polymer Film(s) (PMPC-Graft HD-CLPE)

UHMWPE powder having a molecular weight of approximately 3.5 million and an antioxidant (vitamin E: α-tocopherol) liquid were mixed to prepare mixed powder. The content of vitamin E was 0.1% by mass in UHMWPE. The mixed powder was compaction molded. The compaction-molded body obtained in this way was irradiated with γ rays at a dose of 100 kGy, and then subjected to heat treatment at 123° C. for 12 hours, whereby PE was crosslinked. Then, a sample piece was cut in a disk shape (of 2.5 mm in diameter and 1.0 mm in thickness) from a HD-CLPE obtained by crosslinking PE. The obtained HD-CLPE disk was immersed in a cleaning liquid (a Tween20 (registered trademark) aqueous solution having a concentration of 1.0% by weight) and then cleaned for 12 hours while being stirred. Here, a cleaning temperature was 70° C. After such a cleaning process, the CLPE disk was immersed in an acetone solution (at a concentration of 10 mg/mL) of benzophenone (photopolymerization initiator) for 30 seconds, and then pulled up quickly to thereby remove the solvent from the surface of the HD-CLPE disk. While the HD-CLPE disk was immersed in a MPC aqueous solution (at a concentration of 0.5 mol/L and at a temperature of an aqueous solution of 60° C.), the surface of the HD-CLPE disk was irradiated with ultraviolet rays at an intensity of 5.0 mW/cm² (with a wavelength of 300 to 400 nm) for 90 minutes (1.5 hours). In this way, the polymer film(s) (MPC polymer film(s)) 40 was formed to be graft-polymerized onto the surface of the HD-CLPE disk, and finally, the block was sterilized by irradiation with γ rays at a dose of 25 kGy under the nitrogen atmosphere, thereby producing the sample (iv).

A plurality of pieces of the respective samples (i) to (iv) was prepared, and the relationship between the immersion times into a squalene solution and the oxidative-induction time (OIT) was examined. When immersing the sample in a squalene solution, a liquid temperature of a squalene solution was 120° C. as a temperature condition.

First, the respective samples were immersed in a squalene solution at a concentration of 100% for a predetermined time, thereby providing samples for measurement of the oxidative-induction time (OIT). Then, the oxidative-induction time (OIT) was measured on each sample.

The oxidative-induction time (OIT) was measured based on ASTM D3895-07. Specifically, after increasing the temperature of each sample quickly to 200° C. in the nitrogen gas ($N_2$) atmosphere, the nitrogen gas was switched to oxygen gas ($O_2$). A rise of a heat-generation peak due to the oxidation was confirmed by a differential scanning calorimeter (DSC), and then a time (oxidative-induction time) from switching to the oxygen gas to the rise of the heat-generation peak was measured in each sample.

Figure 8:
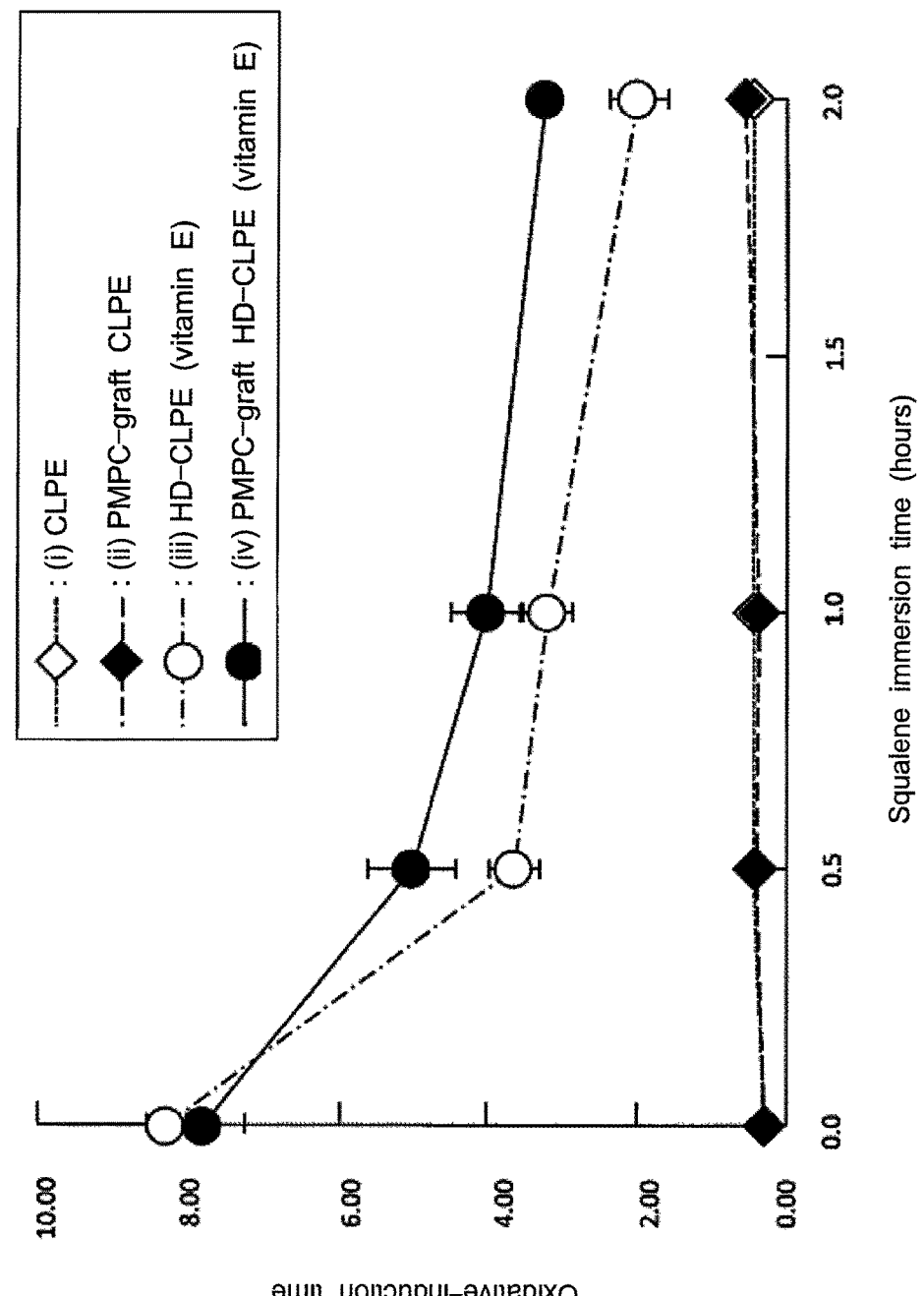
FIG. 8 is a graph showing the result of an oxidative induction experiment in Example 2.

The measurement results are shown in Table 1 and FIGS. 8 and 9.

TABLE 1

Oxidative-induction time (OIT)

| | Squalene immersion time | | | |
|---|---|---|---|---|
| | 0.0 hour (not immersed) | 0.5 hours | 1.0 hour | 2.0 hours |
| Sample (i) | $T_0$ = 0.3 minutes | $T_{0.5}$ = 0.5 minutes | $T_{1.0}$ = 0.45 minutes | $T_{2.0}$ = 0.45 minutes |
| Sample (ii) | 0.3 minutes | 0.5 minutes | 0.35 minutes | 0.55 minutes |
| Sample (iii) | 8.3 minutes | 3.7 minutes | 3.2 minutes | 2.0 minutes |
| Sample (iv) | 7.8 minutes | 5.0 minutes | 4.0 minutes | 3.3 minutes |

Sample for Squalene Immersion Time of 0.0 Hour (not Immersed)

As can be seen from Table 1 and FIG. 8, each of the samples (i) and (ii) not including the antioxidant had an oxidative-induction time of 0.3 minutes even though they were not immersed in squalene, and thus exhibited low antioxidative properties.

The samples (iii) and (iv) including the antioxidant had oxidative-induction times $T_0$ of 8.3 minutes and 7.8 minutes, respectively, when not being immersed in squalene (=immersion time of 0.0 hour), and thus exhibited high antioxidative properties.

When comparing the antioxidative properties of the prosthetic member (corresponding to the sample (iv)) in the present invention with that of the CLPE (corresponding to the sample (i)) used in clinical practice at present, the oxidative-induction time of the sample (i) was 0.3 minutes, whereas the oxidative-induction time of the sample (iv) was 7.8 minutes, which showed that the prosthetic member of the present invention improved its antioxidative properties by 2.6 times. This revealed that the prosthetic member of the present invention could be expected to exhibit 2.6 times as high antioxidative effect as that of the CLPE used in the present clinical practice.

Sample for Squalene Immersion Time of 0.5 Hour

Each of the samples (i) and (ii) not including the antioxidant had an oxidative-induction time of 0.5 minutes for squalene immersion time of 0.5 hours, and thus exhibited low antioxidative properties.

The sample (iii) not having the polymer film(s) had an oxidative-induction time $T_{0.5}$ of 3.7 minutes. The antioxidant properties of this sample relative to that not immersed in squalene was reduced to a half or less as the ratio of $T_{0.5}/T_0$ was 3.7 minutes/8.3 minutes, that is, 45%.

The sample (iv) including the polymer film(s) had an oxidative-induction time $T_{0.5}$=5.0 minutes. The antioxidant properties of this sample relative to that not immersed in squalene could be kept at 50% or more as the ratio of $T_{0.5}/T_0$ was 5.0 minutes/7.8 minutes, that is, 64%.

The oxidative-induction time of the sample (iv) was 5.0 minutes relative to the oxidative-induction time of the sample (i) of 0.5 minutes, so that the sample (iv) improved the antioxidative properties by about 10 times, compared to the sample (i). This showed that the prosthetic member (corresponding to the sample (iv)) in the present invention could be expected to exhibit ten times as high antioxidative effect as that of the CLPE used in the present clinical practice (corresponding to the sample (i)).

Sample for Squalene Immersion Time of 1.0 Hour

The samples (i) and (ii) not including the antioxidant had oxidative-induction times of 0.5 minutes or less (0.45 minutes, and 0.35 minutes, respectively) even for squalene immersion time of 1.0 hour, and thus exhibited low antioxidative properties.

The sample (iii) not having the polymer film(s) had an oxidative-induction time $T_{1.0}$ of 3.2 minutes. The antioxidant properties of this sample relative to that not immersed in squalene was reduced to about 38% as the ratio of $T_{1.0}/T_0$ was 3.2 minutes/8.3 minutes.

The sample (iv) having the polymer film(s) had an oxidative-induction time $T_{1.0}$ of 4.0 minutes. The antioxidant properties of this sample relative to that not immersed in squalene was about 51% as the ratio of $T_{1.0}/T_0$ was 4.0 minutes/7.8 minutes. This sample could maintain the antioxidative properties at 50% or more.

The oxidative-induction time $T_{1.0}$ of the sample (iv) was 4.0 minutes relative to the oxidative-induction time $T_{1.0}$ of the sample (i) of 0.45 minutes, so that the sample (iv) improved the antioxidative properties by about 8.9 times, compared to the sample (i). This revealed that the prosthetic member of the present invention (corresponding to the sample (iv)) could be expected to exhibit 8.9 times as high antioxidative effect as that of the CLPE (corresponding to the sample (i)) used in the present clinical practice.

Sample for Squalene Immersion Time of 2.0 Hour

The samples (i) and (ii) not including the antioxidant had oxidative-induction times of 1.0 minute or less (0.45 minutes and 0.55 minutes, respectively) even after squalene immersion time of 2.0 hours, and thus exhibited low antioxidative properties.

The sample (iii) not having the polymer film(s) had an oxidative-induction time $T_{2.0}$ of 2.0 minutes. The antioxidant properties of this sample relative to that not immersed in squalene was reduced to about 24% as the ratio of $T_{2.0}/T_0$ was 2.0 minutes/8.3 minutes.

The sample (iv) having the polymer film(s) had an oxidative-induction time $T_{1.0}$ of 3.3 minutes. The antioxidant properties of this sample relative to that not immersed in squalene could be kept at a level around a half as the ratio of $T_{1.0}/T_0$ was 3.3 minutes/7.8 minutes, or about 42%.

The oxidative-induction time of the sample (iv) was 3.3 minutes relative to the oxidative-induction time of the sample (i) of 0.45 minutes, so that the sample (iv) improved the antioxidative properties by about 7.3 times, compared to the sample (i). This revealed that the prosthetic member of the present invention (corresponding to the sample (iv)) could be expected to exhibit 7.3 times as high antioxidative effect as that of the CLPE (corresponding to the sample (i)) used in the present clinical practice.

The oxidative-induction times of the respective samples (i) to (iv) in squalene immersion time of 2 hours are shown in FIG. 9. As can be seen from this figure, the samples (i) and (ii) not including the antioxidant had the oxidative-induction time of about 0.5 minutes, whereas
the sample (iii) including the antioxidant had the oxidative-induction time of about 2 minutes. It is found that the presence of the antioxidant enhances the antioxidative properties by about four times. Further, regarding the samples including the antioxidant, the sample (iv) having the polymer film(s) had the oxidant-induction time of 3.25 minutes and had 1.6 times or more as high antioxidative properties as the sample (iii) not having the polymer film(s).

The results of Example 2 revealed that the presence of the antioxidant has been found to drastically improve the antioxidative properties of the sample. Furthermore, the sample including the antioxidant has its surface covered by the polymer film(s), thereby improving oxidation resistance that would otherwise be promoted by the adsorption or absorption of squalene. Even under the environment that causes the sample to come into contact with squalene, the reduction of the antioxidative properties can be suppressed.

DESCRIPTION OF REFERENCE NUMERALS

1 Prosthetic member (cranial bone plate)
2 Substrate
20 Surface of substrate
40 Polymer film(s)
1100 Cranial bone
1101 Defect

The invention claimed is:

1. A cranial bone plate having antioxidative properties comprising:
   a substrate comprising an antioxidant and a polymer material; and
   a polymer film(s) covering a surface of the substrate, the polymer film(s) comprising a (meth)acrylate compound.

2. The cranial bone plate according to claim 1, wherein the polymer film(s) comprises a hydrophilic (meth)acrylate compound.

3. The cranial bone plate according to claim 1, wherein a surface of the cranial bone plate has a squalene index of 0.15 or less that is measured based on a 2 hour squalene immersion.

4. The cranial bone plate according to claim 1, which has an oxidative-induction time of 2 minutes or more, wherein the oxidative-induction time is measured based on a squalene immersion.

5. The cranial bone plate according to claim 4, wherein the cranial bone plate has an oxidative-induction time being 50% or more of an oxidative-induction time of the prosthetic member before being immersed in squalene, wherein the oxidative-induction time is measured based on a 0.5 hour squalene immersion.

6. The cranial bone plate according to claim 4, wherein the cranial bone plate an oxidative-induction time being 30% or more of an oxidative-induction time of the prosthetic member before being immersed in squalene, wherein the oxidative-induction time is measured based on a 2 hour squalene immersion.

7. The cranial bone plate according to claim 1, wherein the polymer material is an ultrahigh molecular weight polyethylene having a molecular weight of $3 \times 10^6$ g/mol or more.

8. The cranial bone plate according to claim 1, wherein the polymer material is a crosslinked polyethylene formed by crosslinking an ultrahigh molecular weight polyethylene having a molecular weight of $3 \times 10^6$ g/mol or more.

9. The cranial bone plate according to claim 1, wherein the antioxidant comprises a lipid-soluble vitamin E group.

10. The cranial bone plate according to claim 1, wherein an additive amount of the antioxidant is in a range of 0.01 to 5% by weight.

11. The cranial bone plate according to claim 1 further comprising:
   a plurality of holes penetrating from an inner surface of the cranial bone plate to an outer surface of the cranial bone plate.

12. The cranial bone plate according to claim 11, wherein at least one of the plurality of holes include a through hole to fix the cranial bone plate to a dura matter, and wherein at least one of the plurality of holes is a screw hole to fix the cranial bone plate to a cranial bone.

13. The cranial bone plate according to claim 12, wherein the through holes are formed on an inner side of the screw holes.

14. The cranial bone plate according to claim 12, wherein the screw holes are on an outer periphery of the cranial bone plate.

15. The cranial bone plate according to claim 14, wherein the through holes are arranged in a vicinity surrounded by the screw holes on the outer periphery of the cranial bone plate.

16. The cranial bone plate according to claim 11, wherein each of the plurality of holes comprises an inner surface covered with the polymer film(s).

* * * * *